(12) United States Patent
Brehm et al.

(10) Patent No.: US 12,186,463 B2
(45) Date of Patent: Jan. 7, 2025

(54) SYSTEM AND METHOD FOR CONNECTING A CONCENTRATE CONTAINER WITH A BLOOD TREATMENT DEVICE WITHOUT LEAKAGES

(71) Applicant: Fresenius Medical Care Deutschland GmbH, Bad Homburg (DE)

(72) Inventors: Winfried Brehm, Hofheim (DE); Philippe Laffay, Sainte Foy les Lyon (FR); Gerhard Wiesen, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 306 days.

(21) Appl. No.: 17/642,268

(22) PCT Filed: Sep. 10, 2020

(86) PCT No.: PCT/EP2020/075375
§ 371 (c)(1),
(2) Date: Mar. 11, 2022

(87) PCT Pub. No.: WO2021/048298
PCT Pub. Date: Mar. 18, 2021

(65) Prior Publication Data
US 2022/0313881 A1    Oct. 6, 2022

(30) Foreign Application Priority Data

Sep. 12, 2019  (CN) .......................... 201910866970.2
Sep. 12, 2019  (EP) ..................................... 19196998

(51) Int. Cl.
*A61M 1/16*   (2006.01)
*A61M 39/26*  (2006.01)

(52) U.S. Cl.
CPC ........ *A61M 1/1668* (2014.02); *A61M 1/1666* (2014.02); *A61M 39/26* (2013.01)

(58) Field of Classification Search
CPC ... A61M 1/1668; A61M 1/1666; A61M 39/26
See application file for complete search history.

(56) References Cited

U.S. PATENT DOCUMENTS 5,540,265 A * 7/1996 Polaschegg ......... A61M 1/1666
                                                604/416
5,806,831 A * 9/1998 Paradis ................. A61M 39/02
                                                604/164.11

(Continued)

FOREIGN PATENT DOCUMENTS

EP     1 344 550      9/2003

OTHER PUBLICATIONS

Chinese Office Action, dated Jul. 5, 2023.

*Primary Examiner* — Jeremy Carroll
(74) *Attorney, Agent, or Firm* — Jacobson Holman PLLC

(57) ABSTRACT

The present invention refers to a container comprising a connection portion allowing for an easy, efficient and more hygienic connection of the container to a fluid dosing unit of a blood treatment device. According to the present invention the fluid dosing unit comprises a valve that fluidically closes the fluid dosing unit if no container is connected to the fluid dosing unit and that opens the fluid dosing unit upon connection of a container to the fluid dosing unit. Thus, undesired spillages potentially arising upon disconnection of the container from the fluid dosing unit can be avoided.

14 Claims, 30 Drawing Sheets

(56) References Cited

U.S. PATENT DOCUMENTS

| | | | | |
|---|---|---|---|---|
| 5,992,455 | A | * | 11/1999 | Koller .................... B67C 3/208 222/145.7 |
| 6,325,115 | B1 | * | 12/2001 | Cowland ................. A01K 5/02 141/346 |
| 2003/0168120 | A1 | * | 9/2003 | Brehm ................ A61M 1/1668 141/313 |
| 2006/0062697 | A1 | * | 3/2006 | Eberle .................. B04B 5/0428 422/548 |
| 2007/0181615 | A1 | * | 8/2007 | Allanson ............. B65D 47/248 222/509 |
| 2013/0245531 | A1 | * | 9/2013 | Brandl ................. A61M 1/169 604/4.01 |
| 2021/0077697 | A1 | | 3/2021 | Brehm et al. |

\* cited by examiner

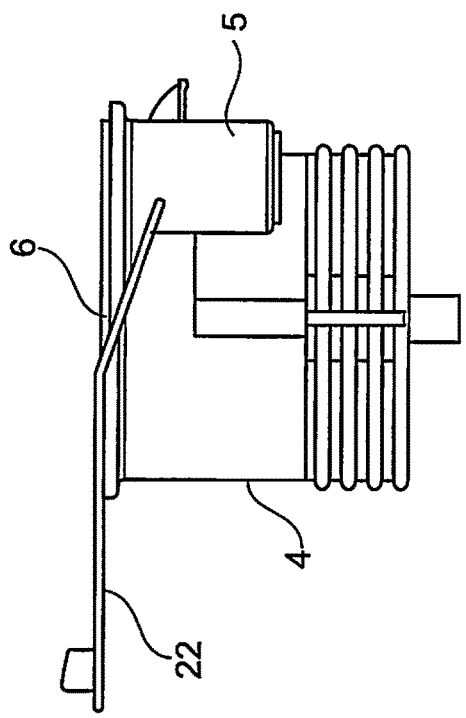
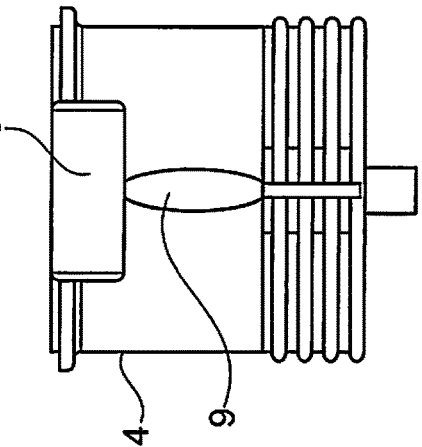
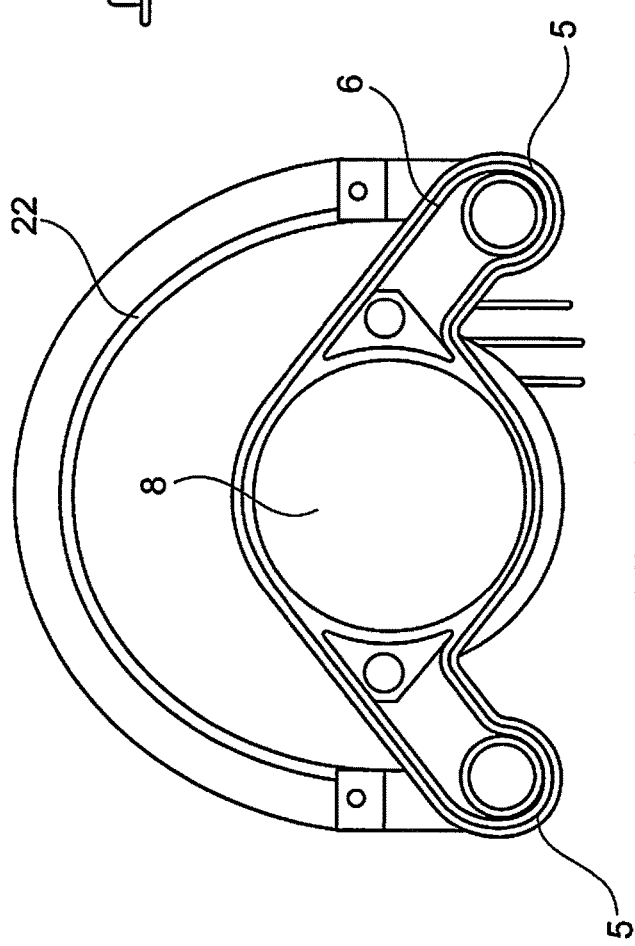
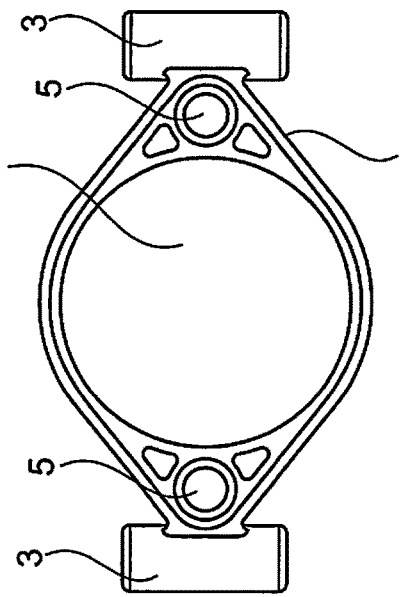
Fig. 12
Fig. 14
Fig. 11
Fig. 13

SYSTEM AND METHOD FOR CONNECTING A CONCENTRATE CONTAINER WITH A BLOOD TREATMENT DEVICE WITHOUT LEAKAGES

The present invention refers to a system and a method for connecting a concentrate container with a blood treatment device and/or a fluid dosing unit. Further aspects of the present invention refer to a container and a fluid dosing unit/blood treatment device, preferably a dialysis machine for renal replacement therapy, configured to be used in a method according to the present invention.

More specifically, the present invention refers to a container comprising a connection portion allowing for an easy, efficient and more hygienic connection of the container to a fluid dosing unit of a blood treatment device. According to the present invention the fluid dosing unit comprises a valve that fluidically closes the fluid dosing unit if no container is connected to the fluid dosing unit and that opens the fluid dosing unit upon connection of a container to the fluid dosing unit.

For chronic blood treatment, especially for chronic dialysis, nowadays almost exclusively bicarbonate-based dialysis solutions are used, that are generated by the blood treatment device itself/online during treatment by diluting an acidic and a basic concentrate, preferably a powder concentrate, with water. Thus, it is established practice that the basic concentrate is generated online during the treatment, i.e. that liquid basic concentrate is continuously generated during the treatment by diluting a dry concentrate/powder concentrate with water.

For this purpose, dry powder concentrate is generally provided in a container that is fluidically coupled to the blood treatment device so that water can be dispensed into the container by the blood treatment device for dissolving the dry concentrate. Simultaneously the basic liquid concentrate/the bicarbonate solution generated in this way is withdrawn by the blood treatment device from the concentrate container. Such a conventional concentrate container is known from e.g. EP1344550.

In conventional blood treatment devices known from the prior art, the concentrate container cannot be connected to the hydraulic system/fluidics system of the blood treatment device during disinfection/rinsing of the blood treatment device.

For this reason, a medical personnel has to connect the concentrate container to the blood treatment device after disinfection/rinsing of the blood treatment device and prior to preparing/priming the extracorporeal circuit of the blood treatment device for treatment.

To connect the concentrate container to the blood treatment device after disinfection/rinsing of the blood treatment device and prior to preparing/priming the extracorporeal circuit of the blood treatment device for treatment, a certain amount of force is necessary to connect the container to the blood treatment device.

In order to make the blood treatment device and the concentrate container as user-friendly as possible, conventionally, the blood treatment machine and the corresponding concentrate container are configured in such a way that a connection element of the container is inserted into a connection element of the machine in a downward movement, so that gravity assists the movement of the connection element of the container into/over the connection element of the machine.

However, this configuration has the disadvantage that because of the opening of the connection element of the container being opened in a downward direction (so that it can be coupled with a corresponding connection element of the blood treatment device by moving the connection element of the container from above in a downwards movement of the connection element of the blood treatment device) after a treatment has ended and the concentrate container is removed from the blood treatment device, liquid concentrate can drip from the connection element of the container.

In addition to that, in blood treatment devices according to the prior art, liquid concentrate can spill, leak or drop from a withdrawal line of the blood treatment device configured to withdraw concentrate from the container upon disconnection of the container from the blood treatment device. Since the liquid concentrate contains solutes, crystallization may occur as an additional disadvantage to these spillages generally not being hygienic.

This liquid concentrate can then collect in the connection element of the blood treatment device causing undesired crystallization and thus potential clogging of the connection element of the blood treatment device.

Thus, it is an object of the present invention to provide a container and/or a system comprising a container and a fluid dosing system/blood treatment device, which avoid such undesired spilling/dripping of liquid concentrate during the removal of the container from the blood treatment device and thus improves hygiene.

This object is solved by the present invention. The present invention uses the container to collect any drops dripping from the connection elements of the blood treatment device and/or prevents such drops/spillages/leakages in the first place. For this purpose, the opening element(s) of a container according to the present invention are preferably opened in an upward direction so that the connection element(s) of the blood treatment device can be inserted into the opening element(s) of the container from above in a downward motion or the container can be moved in an upward motion so that the hat the connection element(s) of the blood treatment device can be inserted into the opening element(s) of the container.

Furthermore, according to the present invention a valve is provided at the fluid dosing unit/blood treatment device that fluidically closes the fluid dosing unit/blood treatment device if no container is connected to the fluid dosing unit/blood treatment device so that no liquid drops from the fluid dosing unit/blood treatment device in the absence of a container.

It is a further advantage of the present invention that the container can be attached to the blood treatment device at an arbitrary point of time so that the blood treatment device is set up correctly for the subsequent connection to the container when desired.

Furthermore, the present invention provides a container that is easier and cheaper to manufacture as fluid flows along connection elements in the form of linear channels through a connection portion of the container from the blood treatment device into the container. In other words, the structure of the connection portion of the container can be simplified in comparison to the prior art in which the fact that the connection portion generally is connected to the blood treatment device via a downward movement dictates a design in which the openings are opened at a lower surface of the connection portion. Thus, according to the prior art fluid flow through the connection portion of the container is not strictly linear/unidirectional but the fluid is diverted in multiple directions which requires a more complex design and more material.

In addition to that, the structure of a container according to the present invention and especially the structure of the connection portion thereof allows filters to be mounted more easily into the openings of a fluid inlet and/or outlet of the container.

A container for concentrate according to an aspect of the invention comprises a main body for containing concentrate, at least one attachment element configured to reversibly attach the container to at least one corresponding attachment element present on a blood treatment device, and at least one connection element, configured to interact with at least one corresponding connection element present on a blood treatment device to fluidically couple the container with the blood treatment device, wherein the at least one attachment element projects in a first direction and the at least one connection element projects in a second direction that is oriented essentially at right angles to the first direction.

According to a preferred embodiment, the first direction in that the at least one attachment element projects is oriented essentially at right angles to the longitudinal axis of the main body of the container. The attachment element of the blood device is inserted into the attachment element of the container preferably along the first direction. If the attachment element of the container is hook-shaped, an attachment element of the blood treatment device that is inserted into the hook-shaped attachment element of the container preferably projects along the first direction.

Furthermore, it has proved advantageous if the second direction in that the at least one connection element projects is oriented essentially in parallel to the longitudinal axis of the main body of the container and the at least one connection element has the form of a hollow cylinder opened at an end surface of the container opposite to the main body of the container and configured to receive a corresponding connection element, e.g. a spout, of the blood treatment device. The at least one connection element of the container preferably has an opening at the flat (top) end surface of the container facing away from the main body of the container.

Preferably, the at least one connection element of the container that can serve as an inlet for conducting fluid into the container or as an outlet for removing fluid from the container projects in a straight line through a connection portion of the container from a flat (top) end surface of the container facing away from the main body of the container to an end surface of the connection portion facing the main body of the container.

Preferably, the container has two connection elements serving as an inlet and an outlet each and each projecting in a straight line through a connection portion of the container from a flat (top) end surface of the container facing away from the main body of the container to an end surface of the connection portion facing the main body of the container.

In the outlet and/or the inlet a fluid permeable actor can be arranged to open a valve in a corresponding connection element of a fluid dosing unit, e.g. a fluid dosing unit of a blood treatment device, upon connection of the container to the fluid dosing unit.

According to one preferred embodiment of the invention, the container comprises two attachment elements each formed as a hook configured to be hooked over a corresponding attachment element present on a blood treatment device that is preferably formed as stud, preferably comprising a circumferential groove, for receiving the hook of the container, thereby to reversibly attach the container to the blood treatment device.

According to an alternative embodiment of the invention the container comprises two attachment elements each formed as a hollow cylinder configured to receive a corresponding attachment element present on a blood treatment device formed as a stud to be inserted into the hollow cylinder of the container, thereby to reversibly attach the container to the blood treatment device.

According to another aspect of the invention the container comprises two connection elements in the form of hollow cylinders opened at an end surface of the container opposite to/facing away from the main body of the container and configured to receive a corresponding connection element, e.g. spout, of the blood treatment device, wherein the spout of the blood treatment device is inserted into each hollow cylinder in a direction projecting from the end surface of the container opposite to the main body of the container towards the main body of the container.

In order to ensure storage stability of concentrate contained within the container, the at least connection element is advantageously sealed by a lid, preferably in the form of a flexible film, that is removably attached to an end surface of the container opposite to/facing away from the main body of the container.

For example, the lid can be glued or welded to the end surface of the container opposite to the main body of the container. When the container is attached and connected to a blood treatment device, the end surface comprising the opening of the at least one connection element of the container preferably is facing the at least one connection element of the blood treatment device and forms a top end surface of the container.

To make the container more user friendly, the flexible film forming the lid preferably comprises a surface configured to be easily peeled from the end surface of the container. In other words, the surface of the flexible film is surface-treated to allow a user to easily peel the flexible film from the end surface of the container thereby to expose the at least one connection element of the container and for example a central opening of the container through that the container can be filled with dry concentrate.

In order to ensure correct mounting of the container to a blood treatment device, the container can be configured to attach to the blood treatment device according to a lock-and-key-configuration. For this purpose, the container can comprise two attachment elements that are formed in different sizes and/or geometrical configurations to allow attachment of the container to a blood treatment device in only one defined mounting position. The blood treatment device in this embodiment preferably comprises two corresponding attachment elements in different sizes and/or geometrical configurations.

Alternatively or additionally, the container or the blood treatment device can comprise two connection elements that are formed in different sizes and/or geometrical configurations to allow fluidic coupling of the container to a blood treatment device in only one defined mounting position. The blood treatment device or the container in this embodiment preferably comprises two corresponding connection elements.

The number of attachment elements and/or connection elements present on the container and/or the blood treatment device is arbitrary and can be varied according to specific applications.

According to a preferred embodiment of the invention, in a connection element of the container a fluid permeable actor is arranged that opens a valve in a corresponding connection element of a fluid dosing unit, for example a fluid dosing unit of a blood treatment device, upon connection of the container to the fluid dosing unit.

For example, the fluid permeable actor comprises a spike that removes a valve body from a valve seat upon connection of the container to the fluid dosing unit. In order to be fluid permeable, the fluid permeable actor preferably comprises at least one lumen to conduct fluid.

Another aspect of the invention refers to a blood treatment device and/or a fluid dosing unit, preferably a blood treatment device comprising a fluid dosing unit, configured to be used with a container according to the present invention.

Such a blood treatment device comprises a main body, at least one attachment element to that a corresponding attachment element of a container for concentrate can be attached, wherein the at least one attachment element is movable relative to the main body in a direction projecting essentially at right angles from a side surface of the main body, and at least one connection element configured to fluidically couple the blood treatment device to a container for concentrate. The main body of the blood treatment device comprises a top surface, a bottom surface and four side surfaces. Depending on the direction of view from a user, a side surface of the blood treatment device can also be referred to as a front surface.

In a preferred embodiment of the invention, the at least one attachment element of the blood treatment device has the form of a pin or stud projecting outward from a side surface of the main body and the at least one connection element has the form of a spout projecting in a direction essentially parallel to the side surface of the main body.

It has proved advantageous if the blood treatment device further comprises a movable and/or motorized guiding element in that preferably a cavity is formed and the at least one attachment element is mounted onto the movable and preferably motorized guiding element. The guiding element can be moved/is movable into a first position, in that the at least one connection element of the blood treatment device, preferably a spout for fluidically connecting the blood treatment device to a container, is received in the cavity present on the guiding element thereby allowing the blood treatment device to be rinsed.

In the first position, the cavity in the guiding element short-circuits and/or closes the internal fluidic circuits of the blood treatment device to form a closed circuit so that rinsing liquid can be circulated in the blood treatment device.

The guiding element can also be moved/is movable into a second position in that the spout is fluidically connected to a container attached to the at least one attachment element of the blood treatment device. The guiding element is preferably movable in the horizontal and/or vertical direction.

In the second position, the guiding element preferably positions the container attached to the at least one attachment element mounted on the guiding element, especially the at least one connection element of the container, relative to the at least one connection element of the blood treatment device so that the container is fluidically coupled to the blood treatment device.

The guiding element can be moved by a motor of the blood treatment device. In this case, movement of the guiding element is preferably automatic. Alternatively, the guiding element may be manually moved. In this case the blood treatment device preferably has a lever or similar structure that allows a user to manually move the guiding element.

Preferentially, the at least one connection element of the blood treatment device, for example, the spout, is movable in a vertical direction essentially parallel to a side surface of the main body of the blood treatment device.

In a preferred embodiment, the at least one connection element of the blood treatment device is movable in a downward direction towards a bottom surface of the main body of the blood treatment device. Additionally or alternatively, the at least one connection element of the blood treatment device is movable in an upward direction towards a top surface of the main body of the blood treatment device.

For example, the at least one connection element of the blood treatment device can be first moved upwards to allow a container attached to the attachment elements to be moved by the guiding element into a position in that the at least one connection element of the blood treatment device and the at least one connection element of the container align in a vertical direction.

Subsequently, the at least one connection element of the blood treatment device can be moved downwards towards the guiding element to fluidically couple the container to the blood treatment device, for example, by inserting the at least one connection element of the blood treatment device into the at least one connection element of the container.

At a later stage, for example, after the concentrate contained in the container has been used up, the at least one connection element of the blood treatment device can be retracted upwards again to withdraw the at least one connection element of the blood treatment device from the at least one connection element of the container to thereby fluidically separate/decouple the container and the blood treatment device from each other.

The blood treatment device preferably further comprises a projection portion present on a side surface of the main body. The guiding element is preferably movable relative to the projection portion in the fashion of a drawer. In other words, the guiding element can be slidably moved relative to the projection portion in a direction essentially at right angles to the side surface of the blood treatment device, i.e. in a horizontal direction.

Preferably, the at least one connection element of the blood treatment device is mounted to the projection portion and can be moved in a direction essentially parallel to the side surface of the blood treatment device to project (preferably in a vertical direction downwards towards the bottom surface of the blood treatment device) out from the projection portion. Further preferably, the at least one connection element of the blood treatment device can be retracted/moved into the projection portion in a vertical direction essentially parallel to the side surface of the blood treatment device.

The movement of the guiding element and/or the at least one connection element of the blood treatment device can be performed automatically or non-automatically, motorized and/or manually.

According to a preferred aspect of the invention, the blood treatment device comprises two attachment elements each formed as a pin/stud, preferably comprising a circumferential groove, for receiving a corresponding attachment element of the container, preferably formed as a hook, thereby to reversibly attach the container to the blood treatment device. The hook can be inserted into the circumferential groove to prevent slipping.

To ensure correct mounting of a container to the blood treatment device in only one possible mounting position, the blood treatment device preferably comprises two attachment elements that are formed in different sizes and/or geometrical configurations to allow attachment of a container to the blood treatment device in only one defined mounting position.

Alternatively or additionally, the blood treatment device can comprise two connection elements that are formed in different sizes and/or geometrical configurations to allow fluidic coupling of a container to the blood treatment device in only one defined mounting position.

To prevent undesired dripping of fluid/liquid from the at least one connection element/connection elements of the blood treatment device, the connection element can be quipped with a valve that closes the connection element if no container is attached to the connection element and opens the connection element if a container is connected to the connection element to fluidically couple the connection element with the container.

In an embodiment of the invention the connection element is a fluid line, for example a supply line or withdrawal line, of a fluid dosing unit, preferably a fluid dosing unit of a blood treatment device. Preferably, the connection element is a withdrawal line of a fluid dosing unit.

Throughout this application, reference is made to a blood treatment device comprising a fluid dosing unit that can be connected to a container comprising dry concentrate to dispense fluid into the container and to withdraw fluid from the container. However, the present invention is not limited to blood treatment devices but can be applied to any fluid dosing unit.

According to a preferred embodiment of the invention the fluid dosing unit comprises a valve in the connection element/fluid line (preferably in a withdrawal line), wherein the valve comprises a valve body that can be moved in an axial direction between a closed position (valve body is in contact with a valve seat) and an open position (valve body is removed from the valve seat). In the open position, fluid can flow from the connection element/fluid line through the valve into the container. The valve is biased into the closed position, for example by means of a spring.

Preferably, the valve is opened by means of a fluid permeable actor arranged in an connection element of the container wherein the connection element serves as an inlet or outlet for fluid into or out of the container. It has proved beneficial to provide the fluid permeable actor in an outlet of the container, because this fluid path contains concentrate (instead of water being dispensed into the container through the inlet) that causes crystallization if the concentrate drips from the connection element/fluid line of the fluid dosing unit. Especially if the fluid line is the withdrawal line through which liquid concentrate (e.g. a bicarbonate solution) flows, crystallization due to spillages is a problem. Another aspect of the present invention refers to a system comprising at least one container according to the present invention and at least one blood treatment device according to the present invention.

Preferably, the container is reversibly attached to the blood treatment device by means of the at least one attachment element present on the container interacting with the at least one attachment element present on the blood treatment device.

Additionally or alternatively, the at least one connection element of the blood treatment device is fluidically coupled to the at least one connection element of the container.

A further aspect of the present invention refers to a method for connecting a container for concentrate, preferably a container according to the present invention, to a blood treatment device, preferably a blood treatment device according to the present invention, comprising the steps:

reversibly attaching the container to the blood treatment device by means of the at least one attachment element present on the container and the at least one attachment element present on the blood treatment device;

moving the container in a horizontal direction/direction projecting essentially at right angles to a side surface of the main body of the blood treatment device towards the main body of the blood treatment device;

moving the container and/or the at least one connection element of the blood treatment device in a vertical direction/direction projecting essentially in parallel to a side surface of the main body of the blood treatment, thereby inserting the at least one connection element of the blood treatment device into the at least one connection element of the container to fluidically couple the container to the blood treatment device.

To prevent uncontrolled dripping of liquid from the at least one connection element of the blood treatment device that can cause contaminations and/or crystallization forming on parts of the blood treatment device, the method may comprise an additional step in that the container is used to capture any liquid drops or spills originating from the at least one connection element of the blood treatment device.

Such additional steps can be, for example:

moving the container and/or the at least one connection element of the blood treatment device in a vertical direction/direction projecting essentially in parallel to a side surface of the main body of the blood treatment, thereby removing the at least one connection element of the blood treatment device inserted into the at least one connection element of the container from the at least one connection element of the container and thereby to fluidically decouple the container from the blood treatment device; and pausing the movement of the container in a position in that the at least one connection element of the container and the at least one connection element of the blood treatment device are at least partially aligned in a vertical direction/direction projecting essentially in parallel to the side surface of the main body of the blood treatment, so that any liquid dripping from the at least one connection element of the blood treatment device is received by the at least one connection element of the container.

In other words, after disconnecting the container from the blood treatment device, the container is not immediately removed but remains for a while vertically below the connection element of the blood treatment device, e.g. a spout, to capture any drops dripping downwards from the connection element.

Furthermore, the method can comprise a rinsing step in that the blood treatment device is rinsed prior to connecting a container to the blood treatment device or after disconnecting the container from the blood treatment device.

In this embodiment, the blood treatment device preferably comprises a movable and/or motorized guiding element comprising the at least one attachment element of the blood treatment device and further comprising a cavity configured to receive the at least one connection element of the blood treatment device. The method further comprises the step:

moving the guiding element into a rinsing position in that the at least one connection element of the blood treatment device is received in the cavity, thereby to fluidically seal the blood treatment device from the outside and allow rinsing of the blood treatment device.

In other words, instead of inserting the connection element of the blood treatment device into the connection element of the container to, for example, dispense water into the container to dissolve concentrate powder to form a liquid concentrate, in the rinsing position, the connection element of the blood treatment device is inserted into the cavity of the guiding element.

Thus, the internal fluidic circuit of the blood treatment device is closed and rinsing fluid can be circulated in the blood treatment device.

Preferably, all method steps apart from the step of reversibly attaching the container to the blood treatment device by means of the at least one attachment element present on the container and the at least one attachment element present on the blood treatment device are performed by the blood treatment device.

This has the advantage that no personnel has to be present to manually connect the container to the blood treatment device. Instead, the container can be attached to the blood treatment device at an arbitrary and convenient time (e.g. during regular working hours) and the blood treatment device establishes a fluid connection between the container and the blood treatment device as needed (on demand) at a specific time point (e.g. during night time) determined for example by a treatment regime.

In other words, the present invention can be described as follows:

An aspect of the invention refers to a container for concentrate, comprising: a main body for containing concentrate, a connection portion having a flat end surface facing away from the main body and an opening through that the main body can be filled with concentrate, an inlet through that fluid can be supplied to the main body and an outlet through that fluid can be withdrawn from the main body, wherein at least in the outlet a fluid permeable actor is arranged that is configured to open a valve in a fluid line of a fluid dosing unit when the container is connected to the fluid dosing unit to fluidically couple the container to the fluid dosing unit.

According to an embodiment of the invention, the fluid permeable actor comprises a spike configured to open the valve and at least one lumen to conduct fluid.

Preferably, the outlet and the inlet each project along a straight line traversing the connection portion from the flat end surface facing away from the main body to a flat end surface facing the main body.

According to another aspect of the invention, the container comprises two attachment elements arranged at two opposing sides of the connection portion and configured to reversibly attach the container to two corresponding attachment elements present on a blood treatment device, wherein the two attachment elements project in a first direction and the outlet and inlet project in a second direction that is oriented essentially at right angles to the first direction.

Preferably, the connection portion is formed handleless and comprises concave gripping portions.

Another aspect of the invention refers to a fluid dosing unit, preferably a fluid dosing unit of a blood treatment device, wherein at least in a fluid line (also referred to as a "withdrawal line") of the fluid dosing device configured to withdraw fluid from a container connected to the fluid dosing unit, a valve is arranged that is configured to fluidically close the fluid line if no container is connected to the fluid dosing unit and further configured to be openable upon connection of a container to the fluid dosing unit to allow fluid to be withdrawn from the container through the valve.

The fluid dosing unit can be part of a blood treatment device, e.g. a dialysis machine for renal replacement therapy.

In a preferred embodiment, the fluid line is a withdrawal line of the fluid dosing unit. However, in principle, the invention could also be applied to a supply line or other fluid line of the fluid dosing unit.

Preferably, the valve comprises an axially movable valve body that is removable from a valve seat upon connection of a container to the fluid dosing unit to allow fluid to be withdrawn from the container and through the valve.

Another aspect of the invention refers to a system comprising at least one container according to the present invention and at least one fluid dosing unit/blood treatment device according to the present invention, wherein preferably the container is reversibly attached to the fluid dosing unit/blood treatment device.

A further aspect of the invention refers to a method for connecting a container for concentrate, preferably a container according to the present invention, to a fluid dosing unit, preferably a fluid dosing unit according to the present invention, comprising the steps:

reversibly attaching the container to the fluid dosing device by means of attachment elements present on the container and attachment elements present on the fluid dosing unit;

moving the container and/or the withdrawal line of the fluid dosing unit rela-tive to each other so that the fluid permeable actor in the outlet of the contain-er opens the valve in the withdrawal line of the fluid dosing unit to fluidically couple the container to the blood treatment device.

The container and/or the withdrawal line of the fluid dosing unit are preferably moved relative to each other so that the fluid permeable actor is inserted into the withdrawal line to move an axially movable valve body away from a valve seat to fluidically couple the container to the fluid dosing unit.

Further features, advantages and technical effects of the present invention become apparent from the drawings showing preferred embodiments of the invention. The drawings merely serve purposes of illustrating the invention but do not purport to limit the invention. In the drawing, same or similar components are denoted by the same reference signs.

In the drawings:

FIG. 11 shows a top view of the connection portion of FIG. 5;

FIG. 12 shows another side view of the connection portion shown in FIG. 5;

FIG. 13 shows a top view of the connection portion of FIG. 6;

FIG. 14 shows a different side view of the connection portion of FIG. 6;

Figure 35:
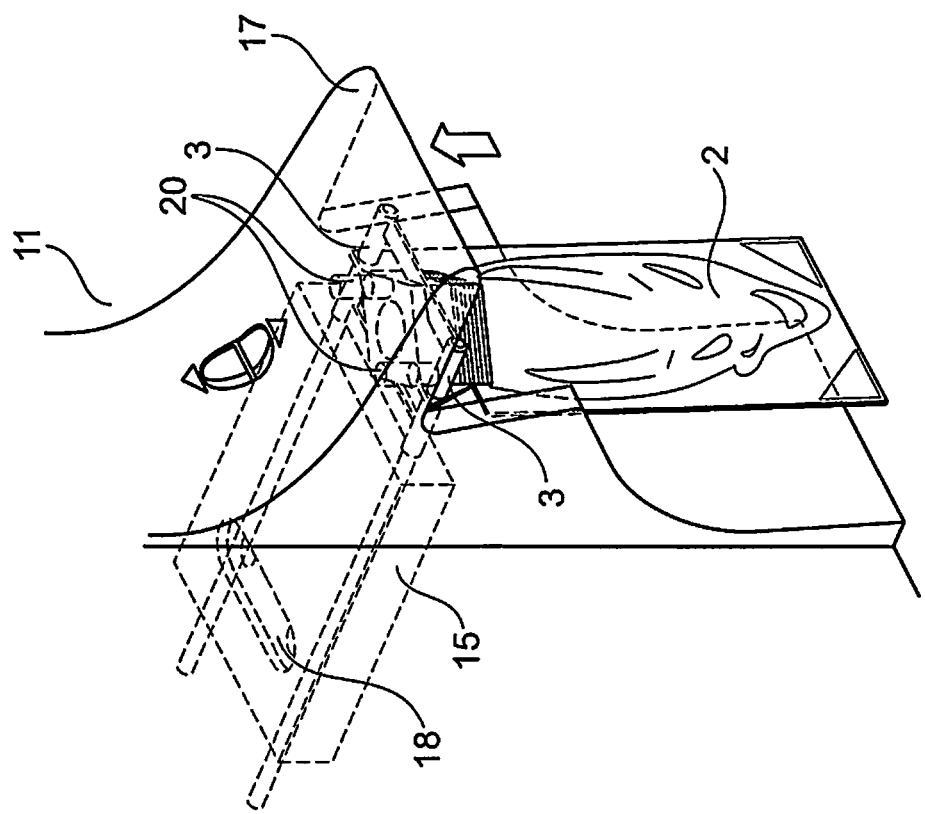
Figure 37:
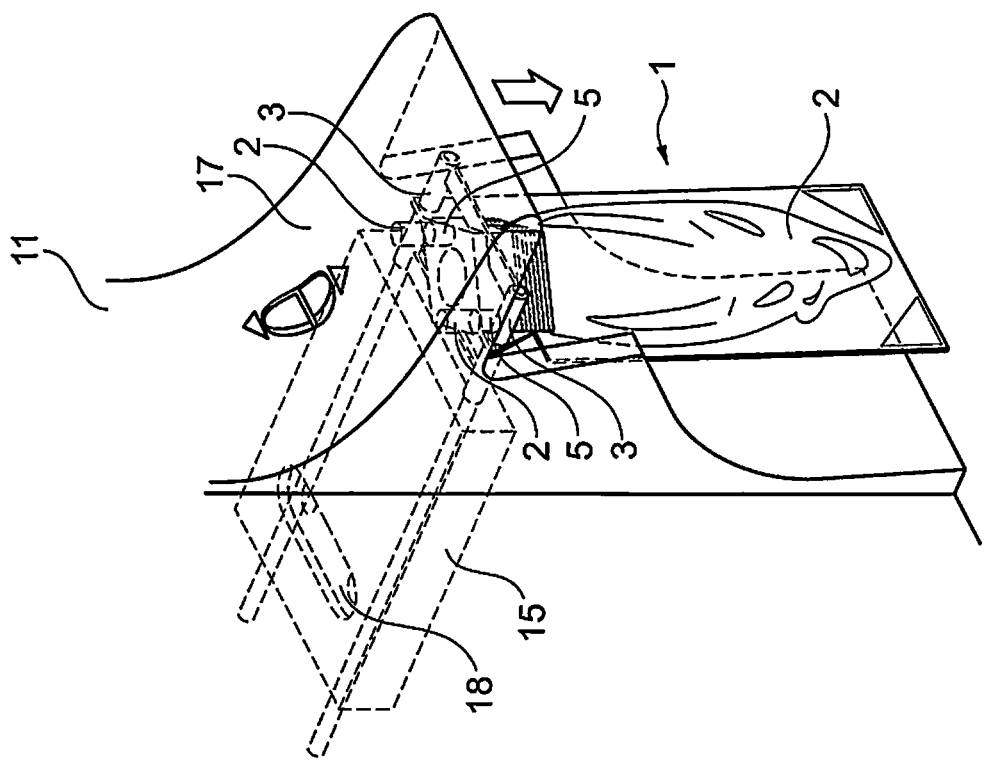
Figure 36:
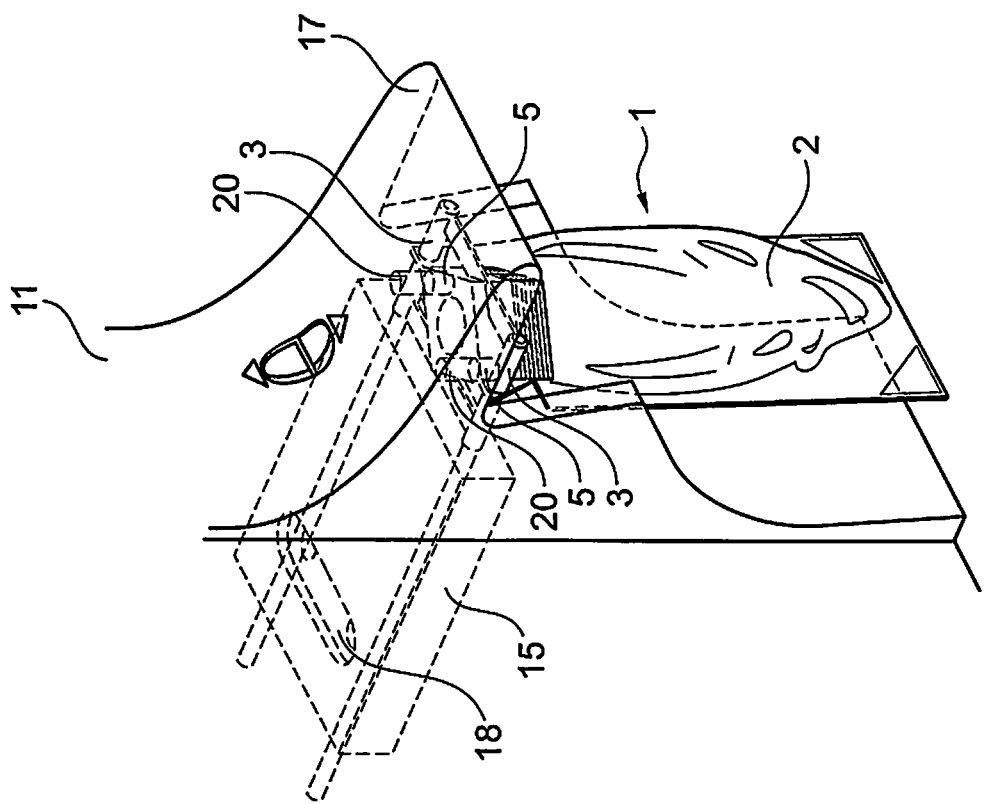
Figure 39:
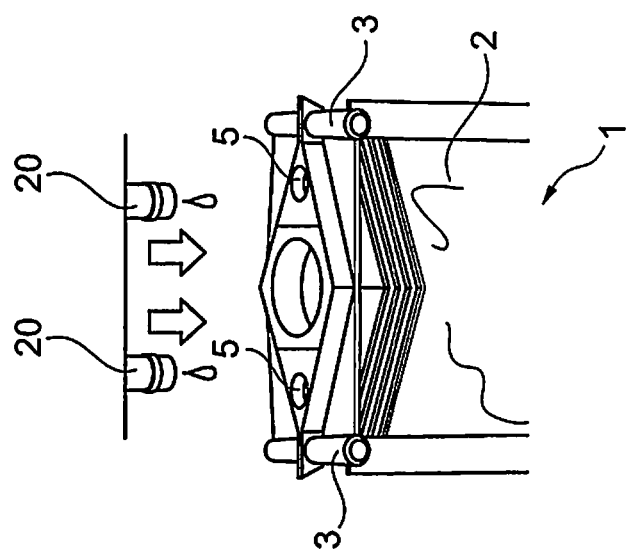
Figure 38:
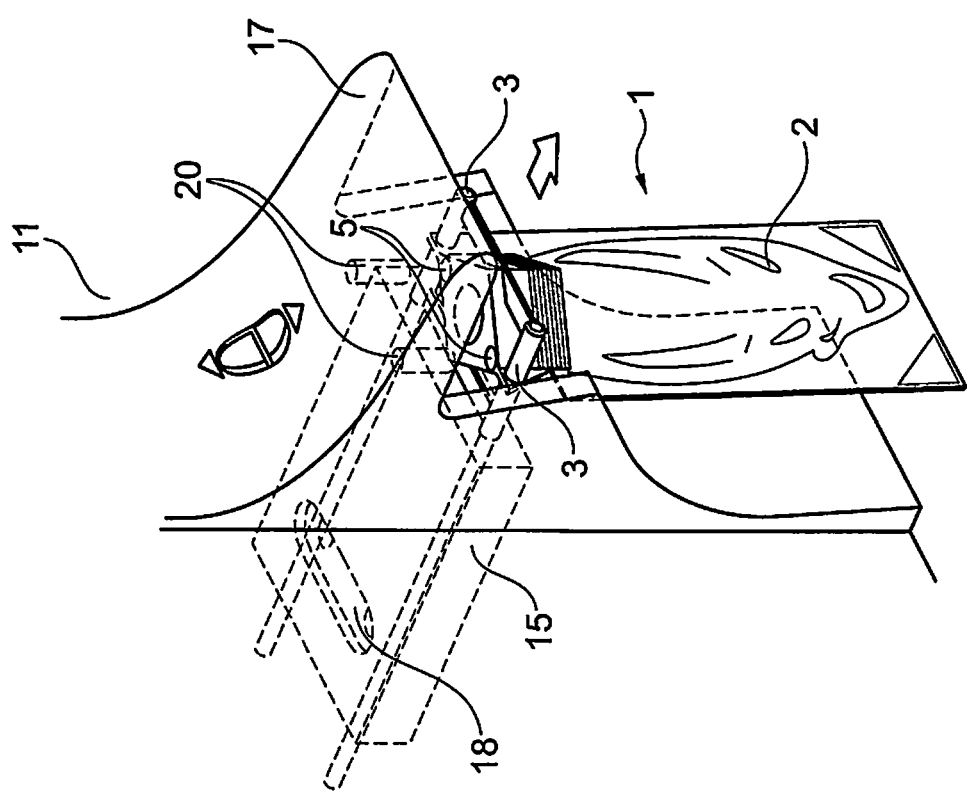
Figure 40:
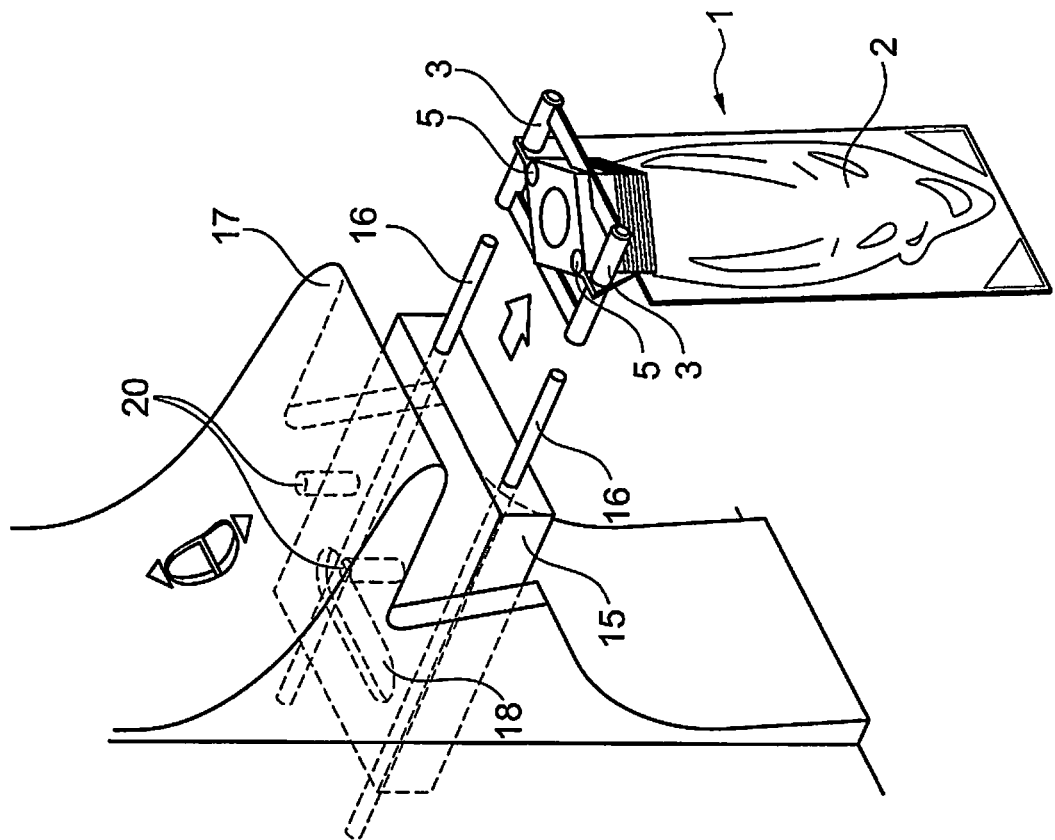
Figure 41:
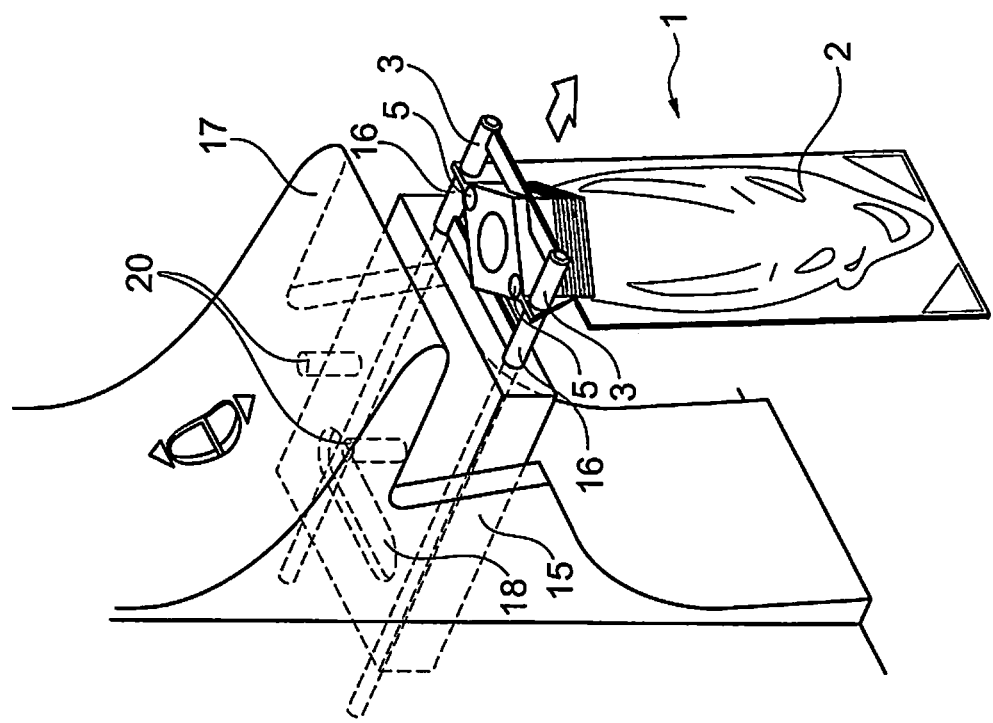
Figure 43:
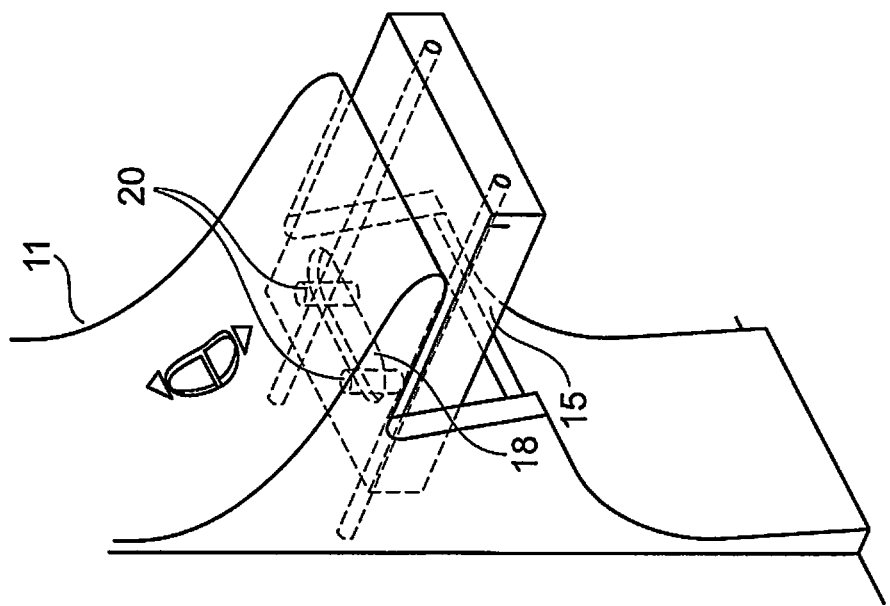
Figure 42:
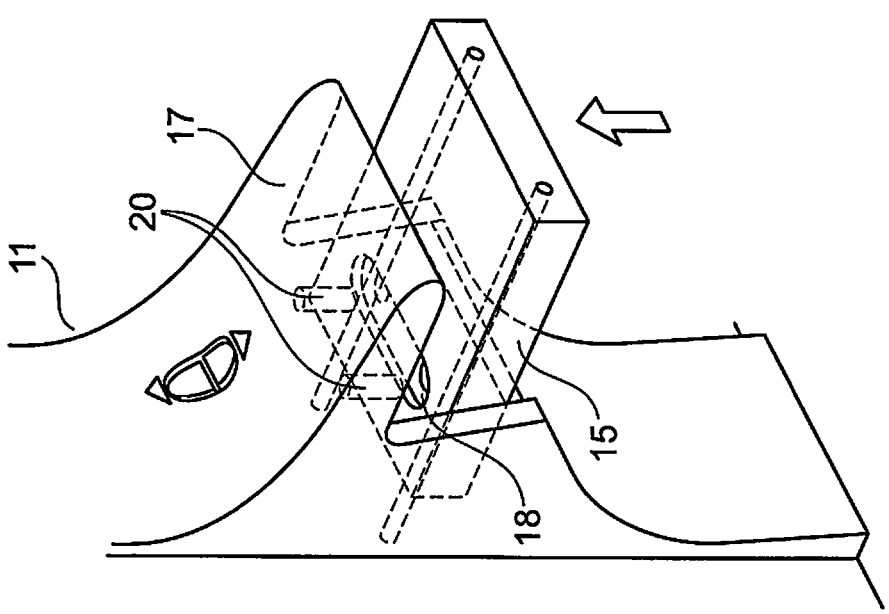

FIG. 35 demonstrates how the container is moved upwards to insert the connection elements of the blood treatment device into the connection elements of the container;

FIG. 36 illustrates the position of the container fluidically connected with the blood treatment device during blood treatment;

FIG. 37 demonstrates how the container is moved downwards after the treatment has ended, to fluidically decouple the connection elements of the container from the connection elements of the blood treatment device;

FIG. 38 shows how the container is held in a position, in that the connection elements of the blood treatment device and the container are fluidically coupled but aligned in a vertical direction;

FIG. 39 illustrates how droplets dripping from the connection elements of the blood treatment device are captured by the concentrate bag;

FIG. 40 demonstrates how after completion of the treatment the container is removed from the blood treatment device by moving the container away from a side surface of the blood treatment device;

FIG. 41 how after completion of the treatment the container is detached from the blood treatment device;

FIG. 42 demonstrates how the guiding element is then moved into the rinsing position by aligning the cavity present on the guiding element in a vertical direction with the connection elements of the blood treatment device; and FIG. 43 illustrates the guiding element in the rinsing position in that the connection elements are inserted into the rinsing cavity present in the guiding element.

Figure 44:
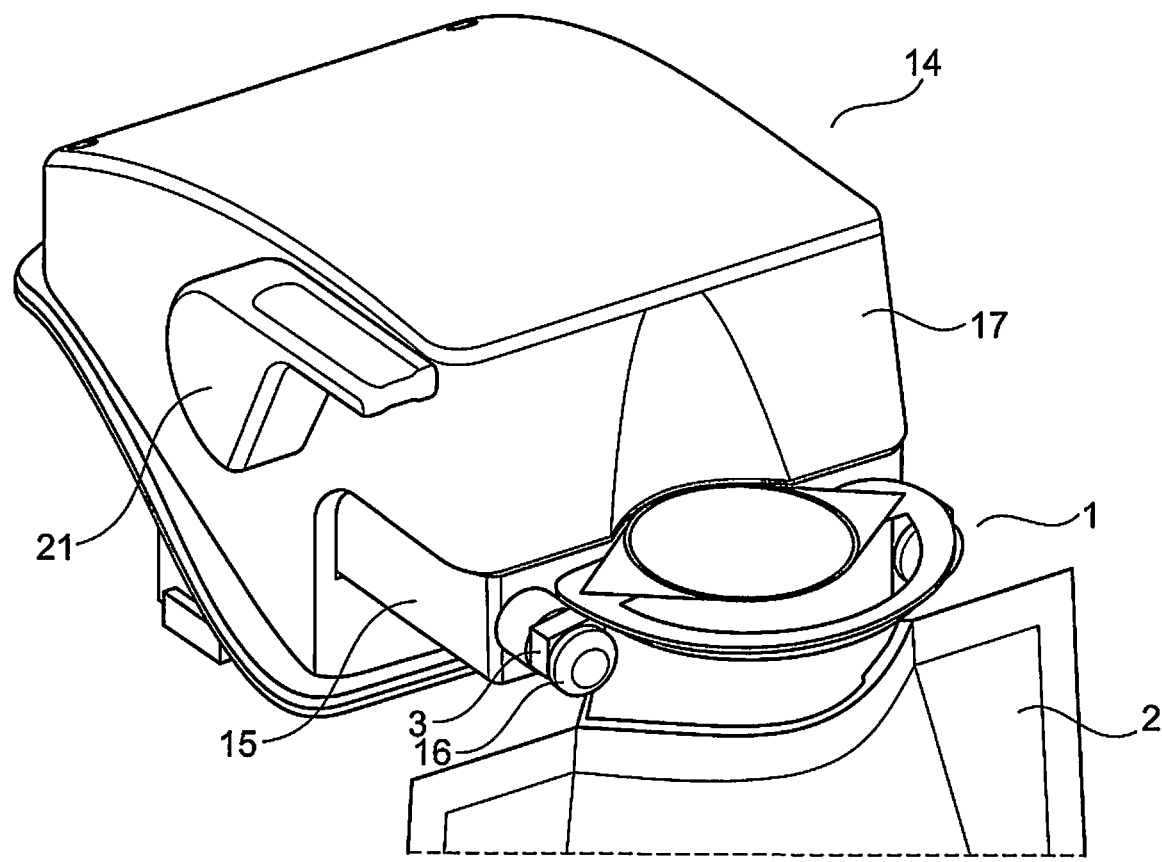

FIG. 44 shows an embodiment in which the guiding element can be manually moved using a lever 21.

Figure 45:
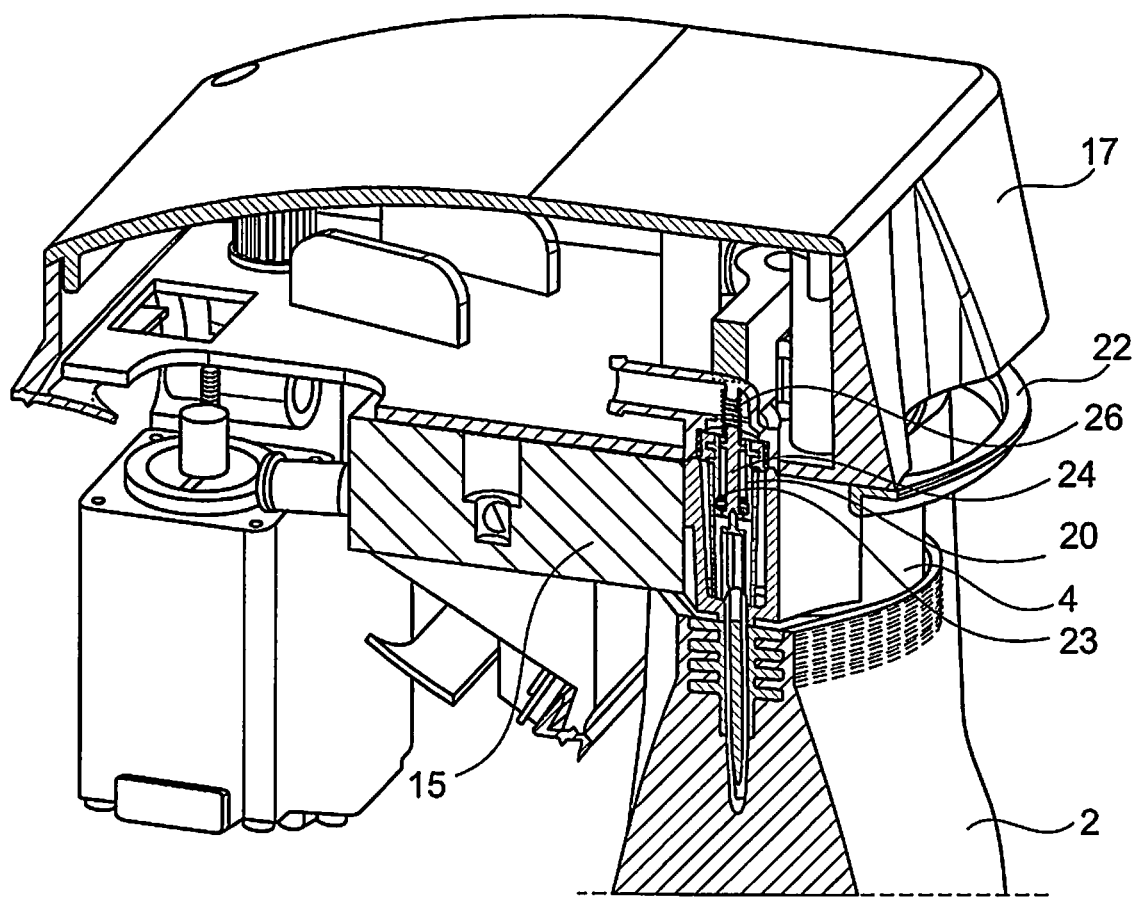

FIG. 45 shows a sectional view of an embodiment in that the fluid dosing unit of a blood treatment device is equipped with an integrated valve to prevent fluid from dripping from the fluid dosing if no container is connected to the fluid dosing unit.

Figure 47:
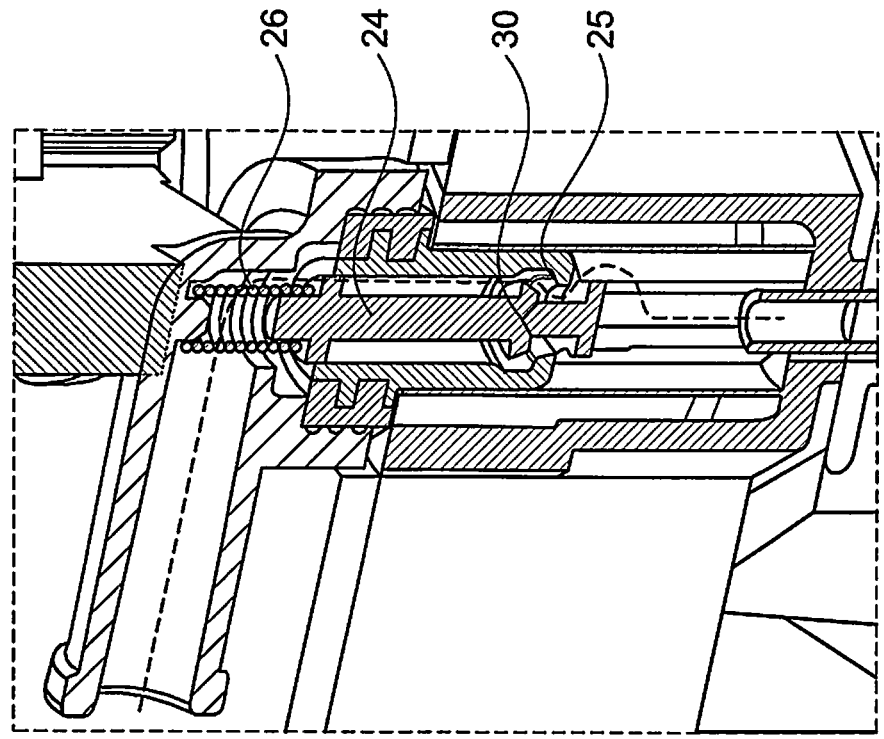
Figure 46:
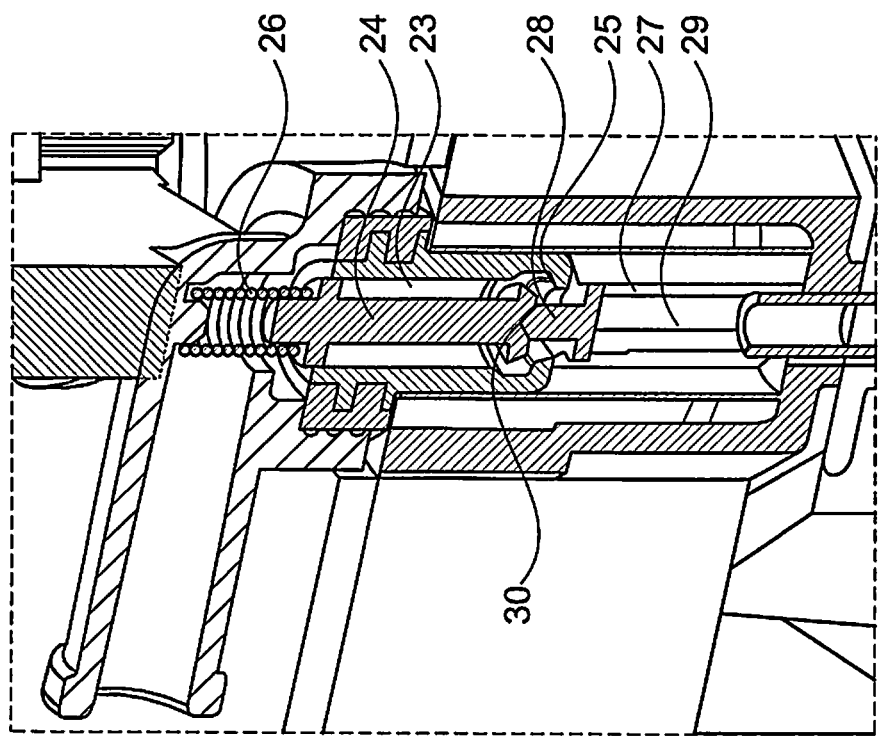

FIGS. 46 and 47 show sectional views of the embodiment auf FIG. 45 in a state in that a container is connected to the fluid dosing unit and the valve is open.

Figure 48:
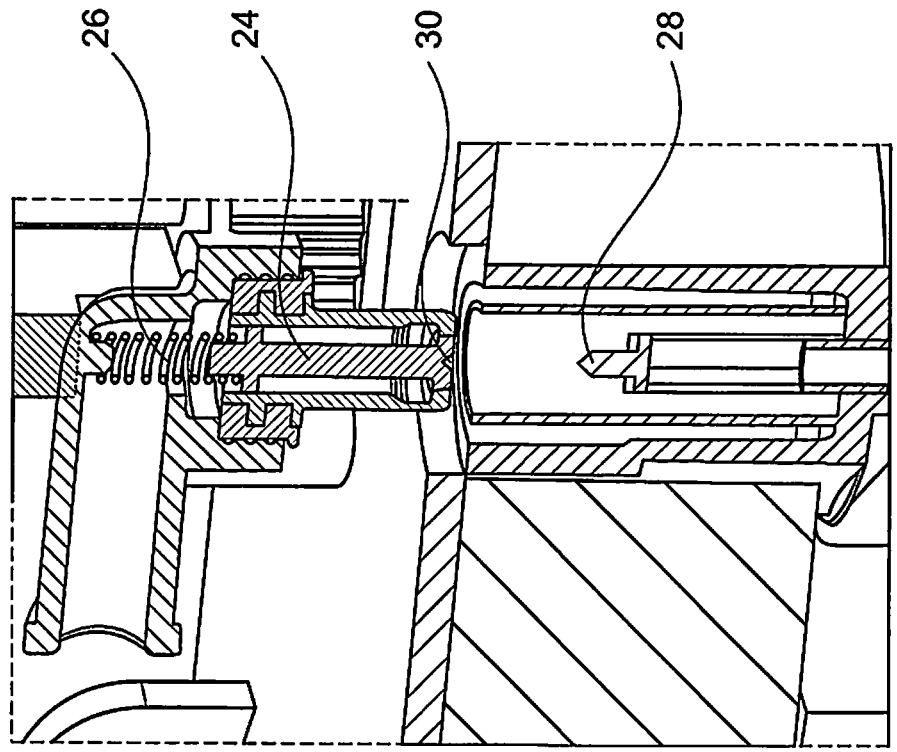
Figure 48:
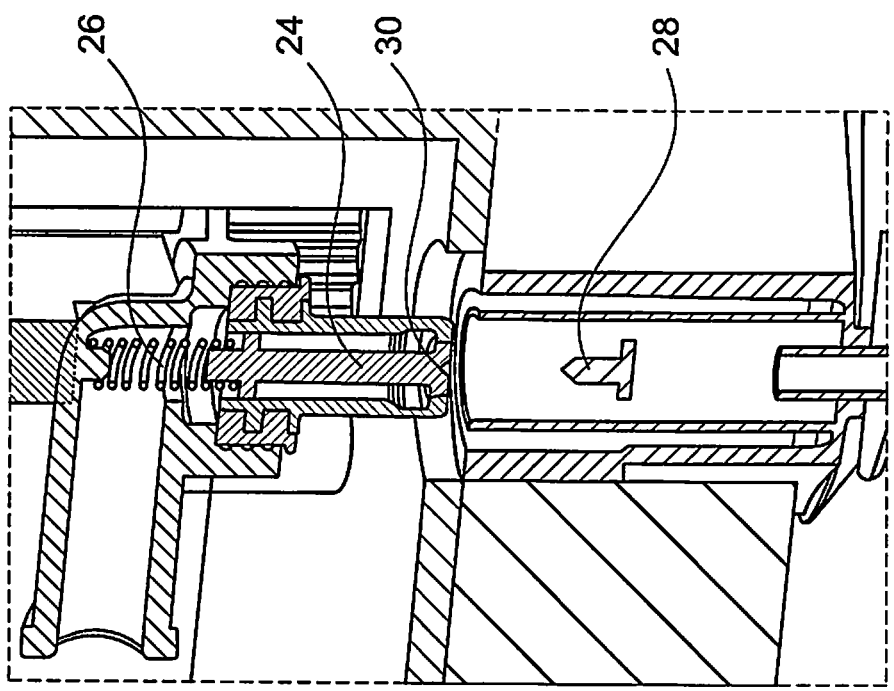

FIG. 48 shows sectional views of the embodiment auf FIG. 45 in a state in that no container is connected to the fluid dosing unit and the valve is closed.

Figure 49:
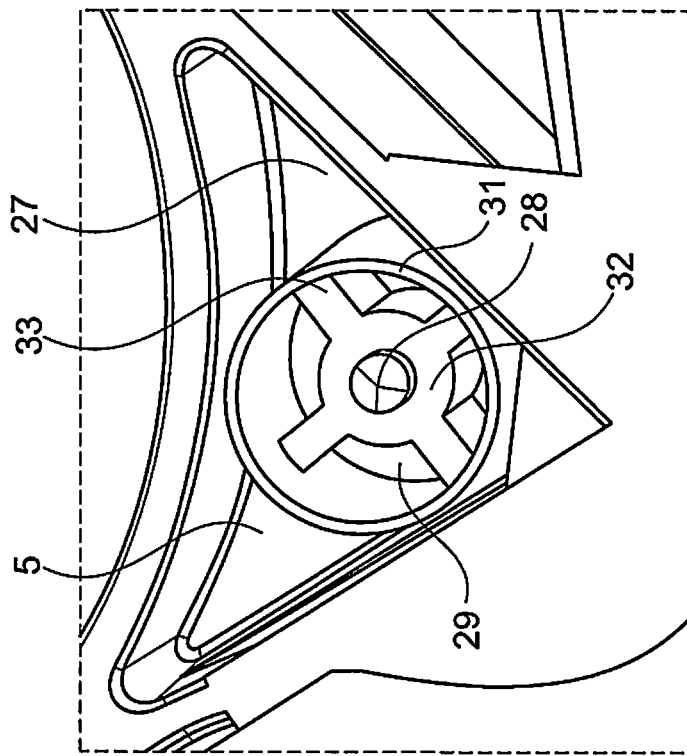

FIG. 49 shows a detailed view of a fluid permeable actor that can be provided at a container according to the present invention to open the valve of the fluid dosing unit shown in FIG. 45.

Figure 50:
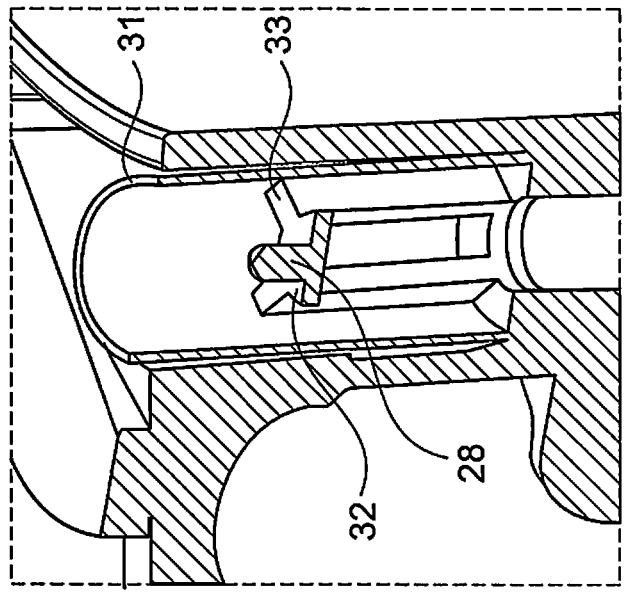

FIG. 50 shows a sectional view of the fluid permeable actor of FIG. 49.

Figure 1:
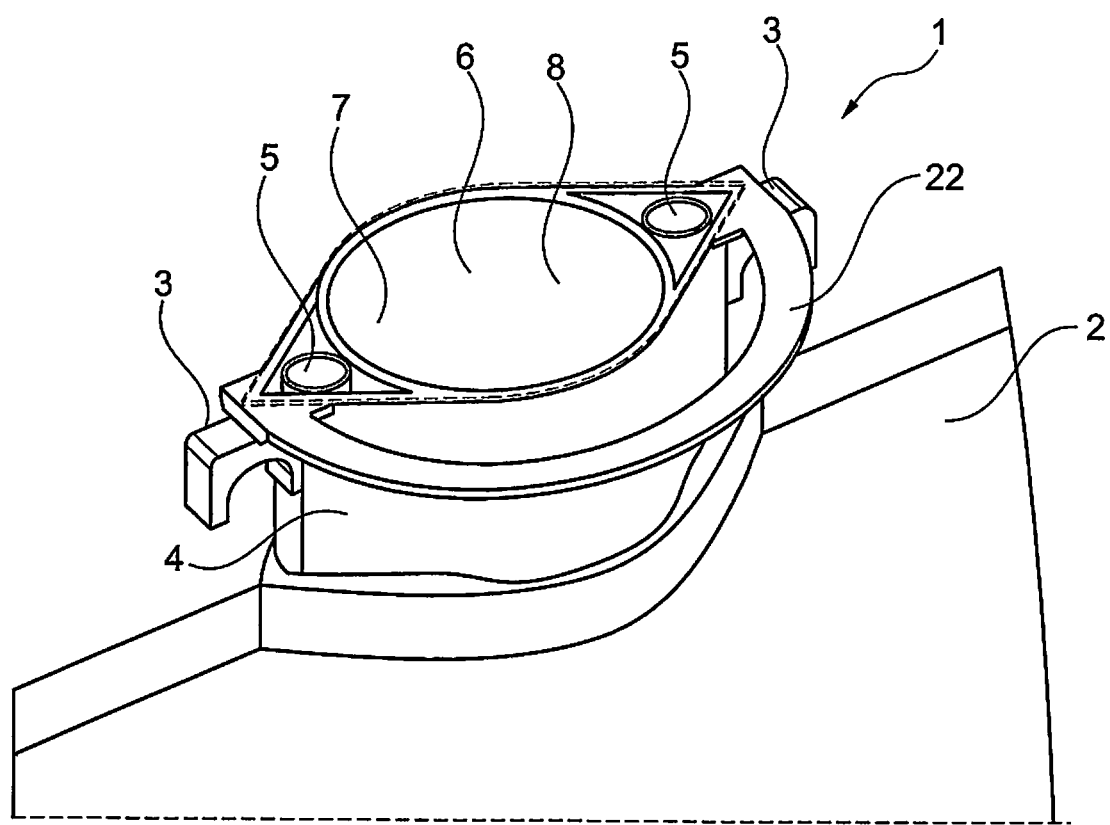
FIG. 1 shows an embodiment of a container according to the present invention.

As shown in FIG. 1, a container 1 comprises a main body 2 configured to contain a dry and/or liquid concentrate. Furthermore, the container 1 comprises two attachment elements 3 having the form of hooks that are arranged at opposite sides of an attachment portion 4 of the container 1.

Furthermore, the container 1 comprises connection elements 5 that are opened towards a flat top end surface 6 of the connection portion 4 of the container 1 that is opposite to/facing away from the main body 2. In this embodiment, the container also comprises a handle 22 allowing a user to grip the container 1. The top end surface 6 is sealed by a flexible film 7 that covers the connection elements 5 as well as the central opening 8 of the connection portion 4.

Figure 2:
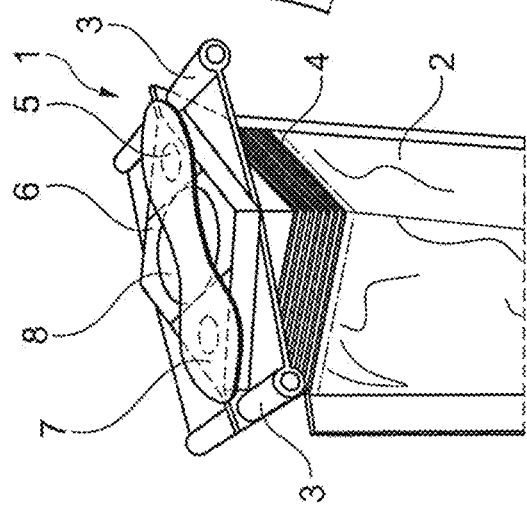
FIG. 2 shows another embodiment of a container according to the present invention that comprises a peelable, flexible film to seal the connection elements of the container.

FIG. 2 shows another container 1 according to the present invention. In this embodiment the flexible film seals the connection element 5 but does not completely cover the central opening 8. Furthermore, in this embodiment, the attachment elements 3 take the form of hollow cylinders configured to receive corresponding studs/pins of a blood treatment device.

Figure 3:
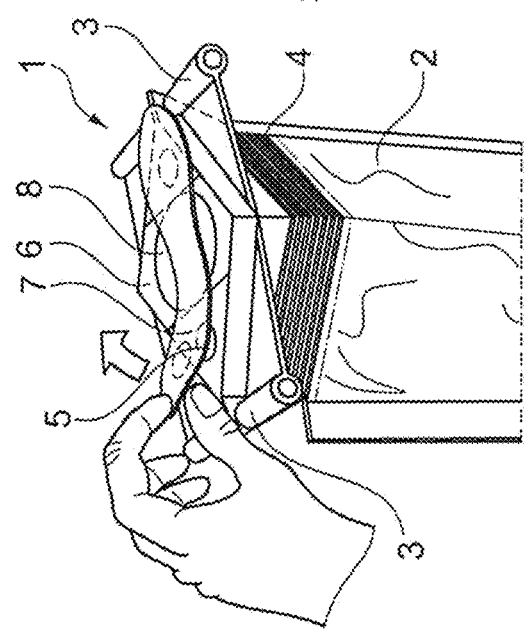
FIG. 3 shows how a user can peel the flexible film from the end surface of the container.

FIG. 3 shows a user peeling off the flexible film 7 from the top end surface 6 of the container 1. As in all drawings, components denoted by the same reference numerals are the same or similar components.

Figure 4:
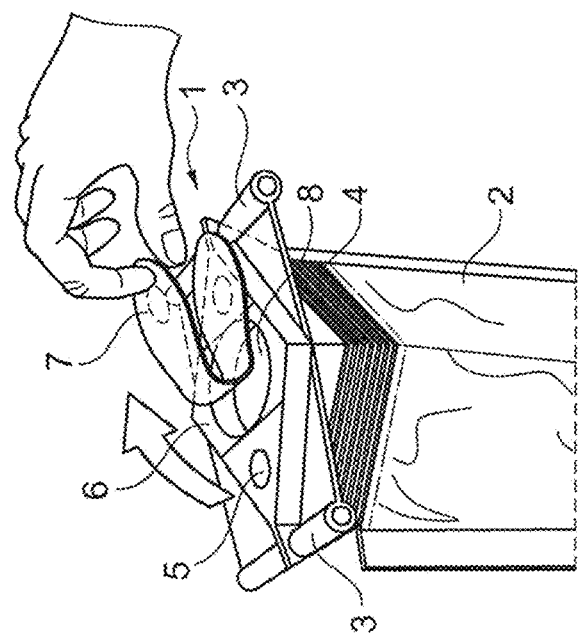
FIG. 4 shows a state in which the user has almost completely removed the flexible film from the top end surface of the container.

In the state shown in FIG. 4, the user has almost completely removed the flexible film 7 from the top end surface 6 of the container 1.

Figure 5:
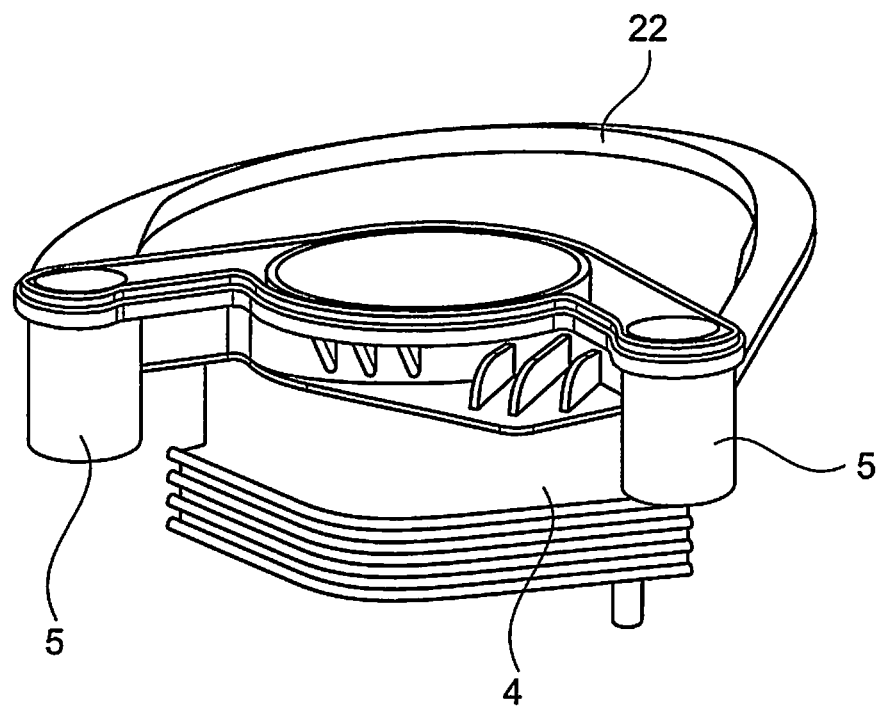
FIG. 5 shows a connection portion of a concentrate container according to the prior art.

FIG. 5 shows a connection portion 4 of a concentrate container known from the prior art. Such conventional connection portions of containers known from the prior art generally comprise connection elements 5 that are opened downwards so that liquid can drip from these connection portions into connection elements present on the blood treatment device that are configured to be inserted into the connection elements 5. The connection portion further comprises a handle 22 allowing a user to grip the connection portion.

Figure 6:
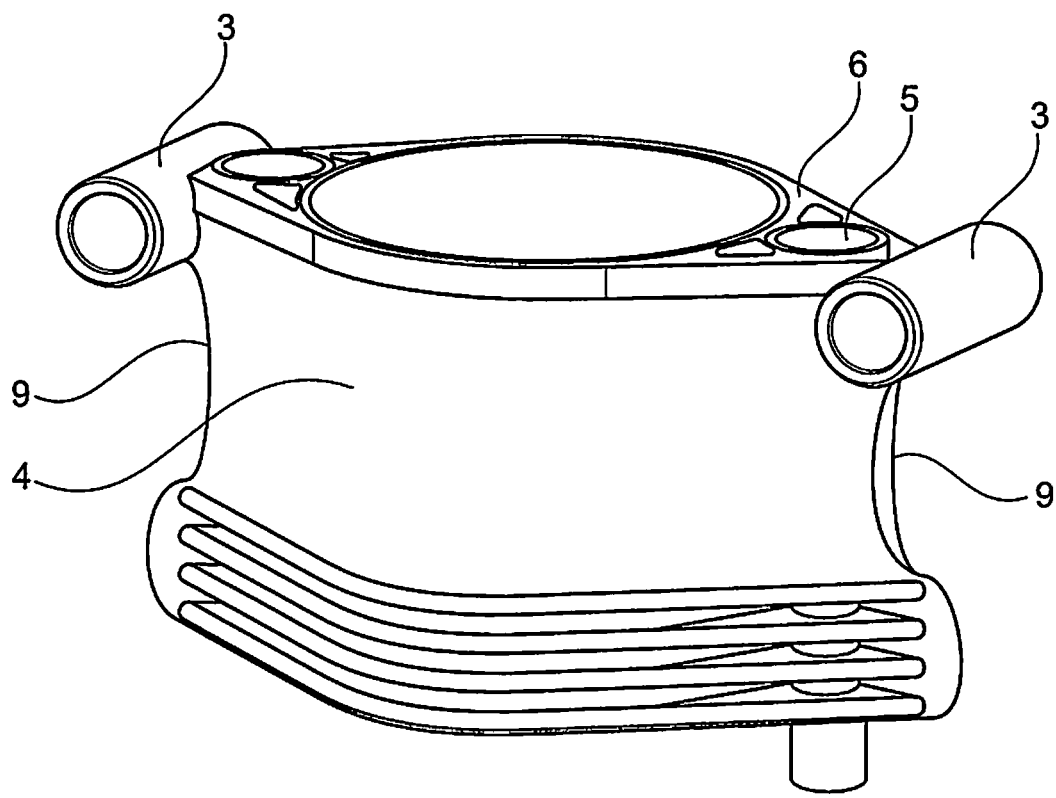
FIG. 6 shows a connection portion of a container according to an embodiment of the present invention.

FIG. 6 shows a connection portion 4 of the container according to the present invention. This connection portion comprises attachment elements 3 formed as hollow cylinders and configured to receive corresponding connection elements, especially in the form of studs, pins or cylinders, present on the blood treatment device.

The connection portion 4 further comprises connection elements 5 that are opened upwards towards a top end surface 6 of the connection portion.

According to this embodiment, the connection portion 4 furthermore comprises gripping portions 8 at opposing sides of the connection portion 4 that replace the handle 22 present in the conventional connection portion shown in FIG. 5.

Figure 7:
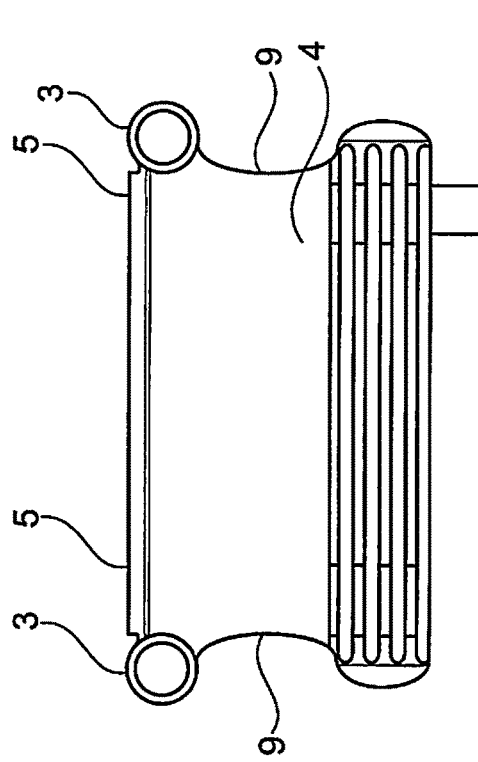
FIG. 7 shows a side view of the connection portion of FIG. 5.
Figure 8:
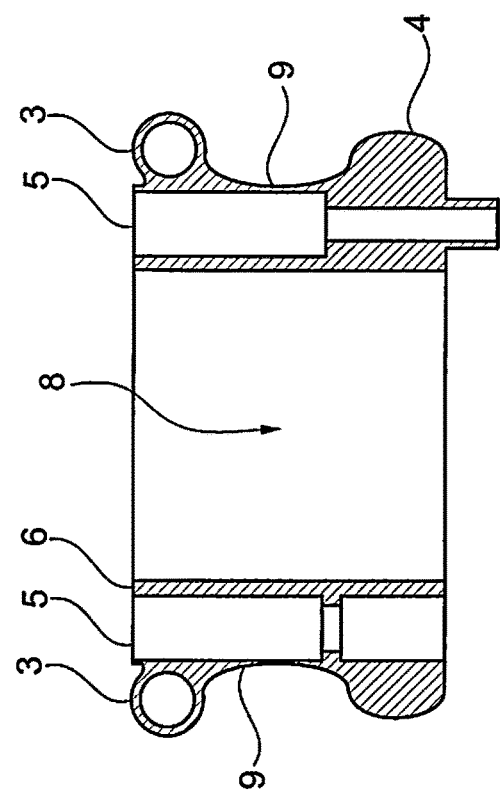
FIG. 8 shows a side view of the connection portion of FIG. 6.

FIG. 7 shows the connection portion 4 according to the prior art in a side view, showing the connection elements 5 as well as the handle 22. In comparison to that, the connection portion 4 of the container according to the present invention shown in FIG. 8 comprises attachment elements 3 arranged at opposing sides of the connection portion 4 and formed as hollow cylinders. The openings of the connection portions cannot be seen in this view.

Figure 9:
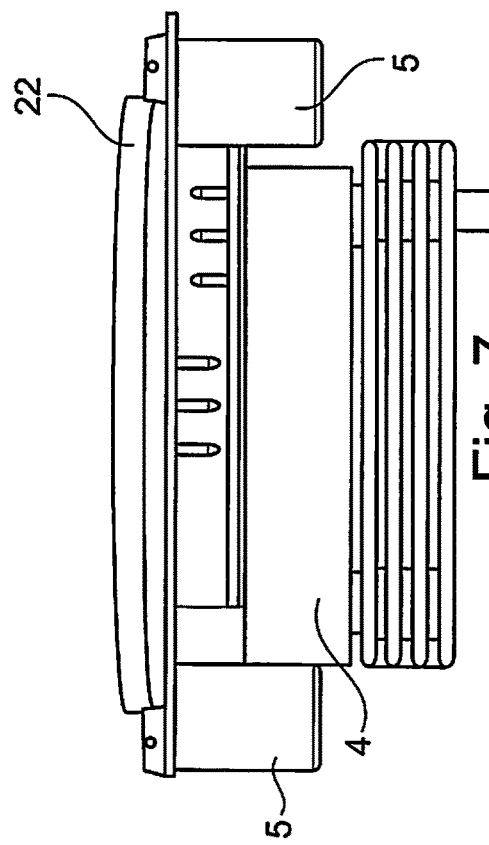
FIG. 9 shows a sectional view of the connection portion of FIG. 7.
Figure 10:
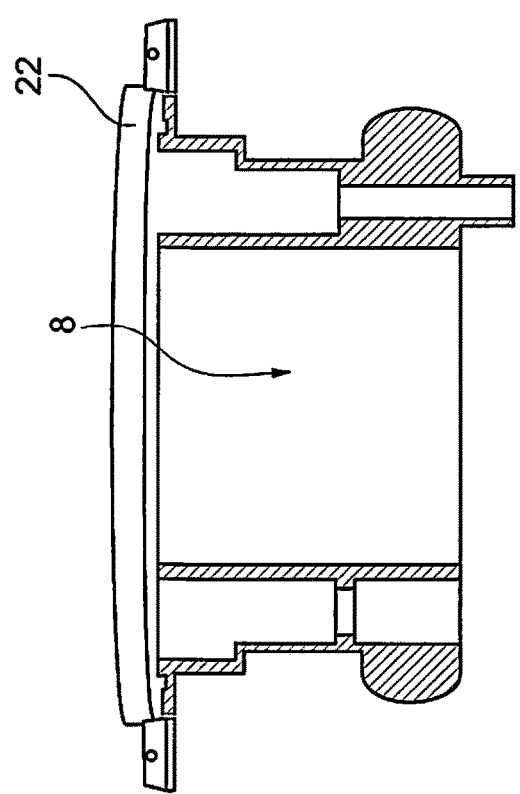
FIG. 10 shows a sectional view of the connection portion of FIG. 8.

FIG. 9 shows a sectional view of the connection portion 4 of FIG. 7 in that the handle 22 is clearly visible. In the sectional view of the connection portion 4 according to the present invention in FIG. 10, the gripping portions 9 are clearly visible as well as the attachment elements 3 and the connection elements 5 that are opened towards a top end surface 6 of the connection portion 4.

As can be seen from FIG. 11, the connection elements 5 of the connection portion 4 according to the prior art also function as attachment elements, because the connection elements 5 in the form of hollow cylinders are arranged over corresponding spouts of the blood treatment device.

This is further illustrated in the view of FIG. 12, from that it can be seen that attachment elements of the blood treatment device, i.e. connection elements of a blood treatment device according to the prior art are inserted into the connection elements 5 of the connection portion 4 in an essentially vertical position/direction in FIG. 12, thereby allowing liquid from the connection elements 5 to drip out of the connection elements 5 of the connection portion 4 of a container 1.

As shown in FIG. 13, according to the present invention, the attachment elements 3 and the connection elements 5 are separate from each other. From FIG. 13 it can also be easily seen, that the attachment elements 3 and the connection elements 5 are arranged relative to each other in that they project along directions that are essentially arranged at right angles to each other, preferably horizontally and vertically respectively. In the example of FIG. 13, the attachment elements project in a direction from the top of FIG. 13 to the bottom of FIG. 13 whereas the connection elements 5 are openings projecting or extending in the direction into and out of the paper plane.

FIG. 14 provides another clear view of the gripping portion 9, that can substitute the handle 22 present in connection portions 4 known from the prior art.

Figure 15:
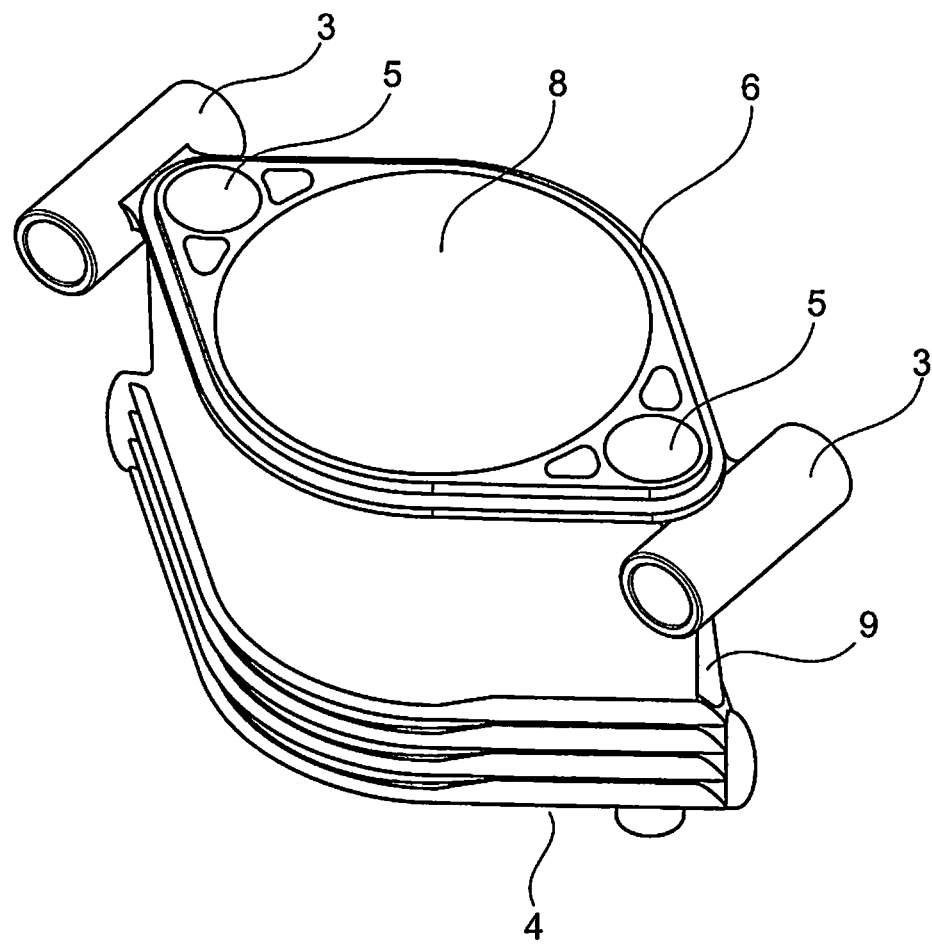
FIG. 15 shows a perspective top view of the connection portion of FIG. 6.

FIG. 15 further illustrates how the direction of extension of the attachment elements 3 is arranged essentially at right angles to the direction of extension of the connection elements/openings 5.

Figure 16:
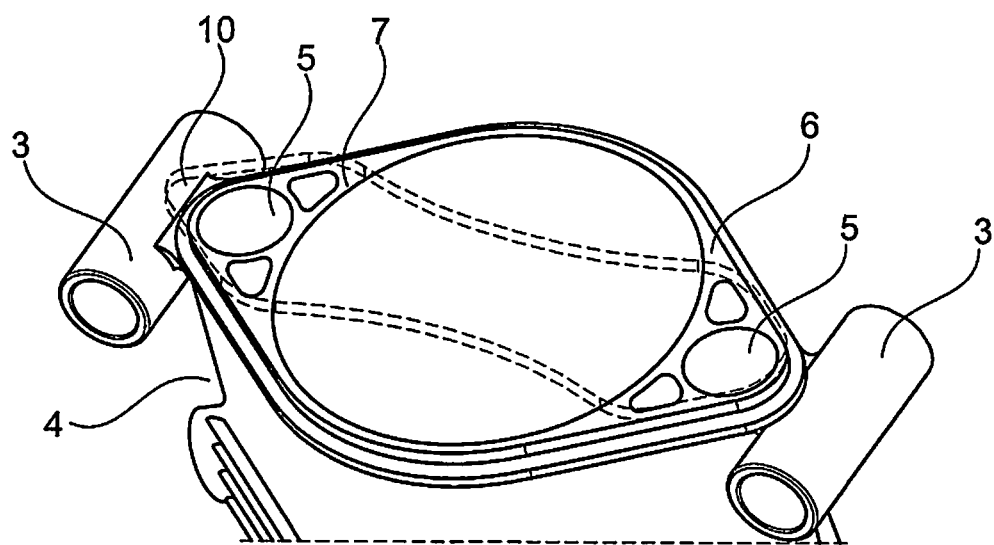
FIG. 16 shows a detailed view of the connection portion of FIG. 6 that is sealed by a flexible film.

As can be seen in FIG. 16, the connection elements 5 are preferentially sealed off by the flexible strip 7 that is preferentially welded to the top end surface 6 of the connection portion 4 to close the connection elements 5.

Preferentially, the flexible film 7 comprises a gripping section 10 that allows the user to grip the flexible film 7 to remove the flexible film 7 from the top end surface 6 of the connection portion 4 of container 1.

Figure 17:
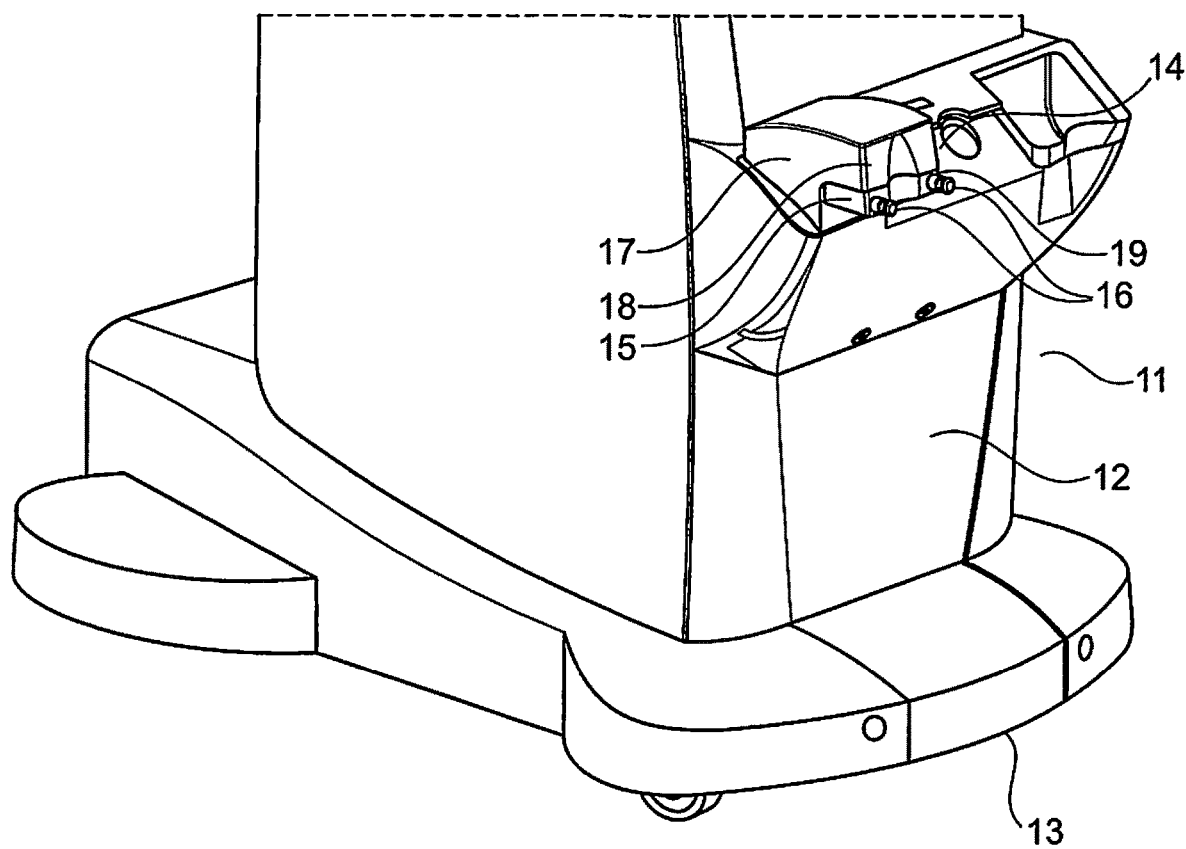
FIG. 17 shows a blood treatment device according to the present invention comprising two attachment elements.

As can be seen in FIG. 17, a blood treatment device 11 according to the present invention includes a main body 12 that has a bottom surface 13 and a attachment assembly 14 configured for attaching to and connecting to the container 1.

The attachment assembly 14 comprises a guiding element 15 to which two attachment elements 16 are mounted that in this embodiment have the form of protruding cylinders/studs/pins each having a circumferential groove into which the hooks or hook-shaped attachment elements 3 of a container 1 can be inserted.

The attachment assembly 14 furthermore comprises a projection portion 17. In the configuration shown in FIG. 17, a front surface 18 of the projection portion 17 and front surface 19 of the guiding element 15 are aligned with each other to form a continuous front surface of the attachment assembly 14. This corresponds to the rinsing position.

Figure 18:
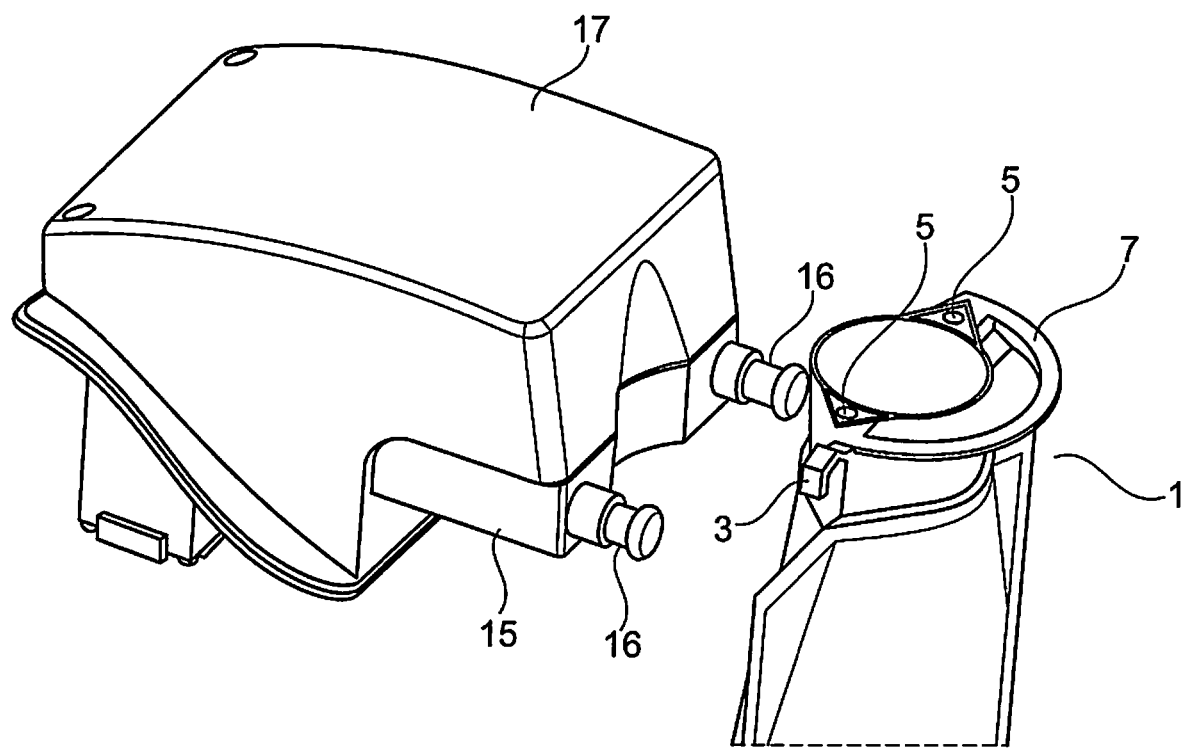
FIG. 18 shows how a container is attached to the attachment elements of the blood treatment device of FIG. 17.

As can be seen in FIG. 18, a bag 1 can be attached by means of hook shaped attachment elements 3 onto the stud-shaped attachment elements 16 mounted onto the guiding element 15.

Figure 19:
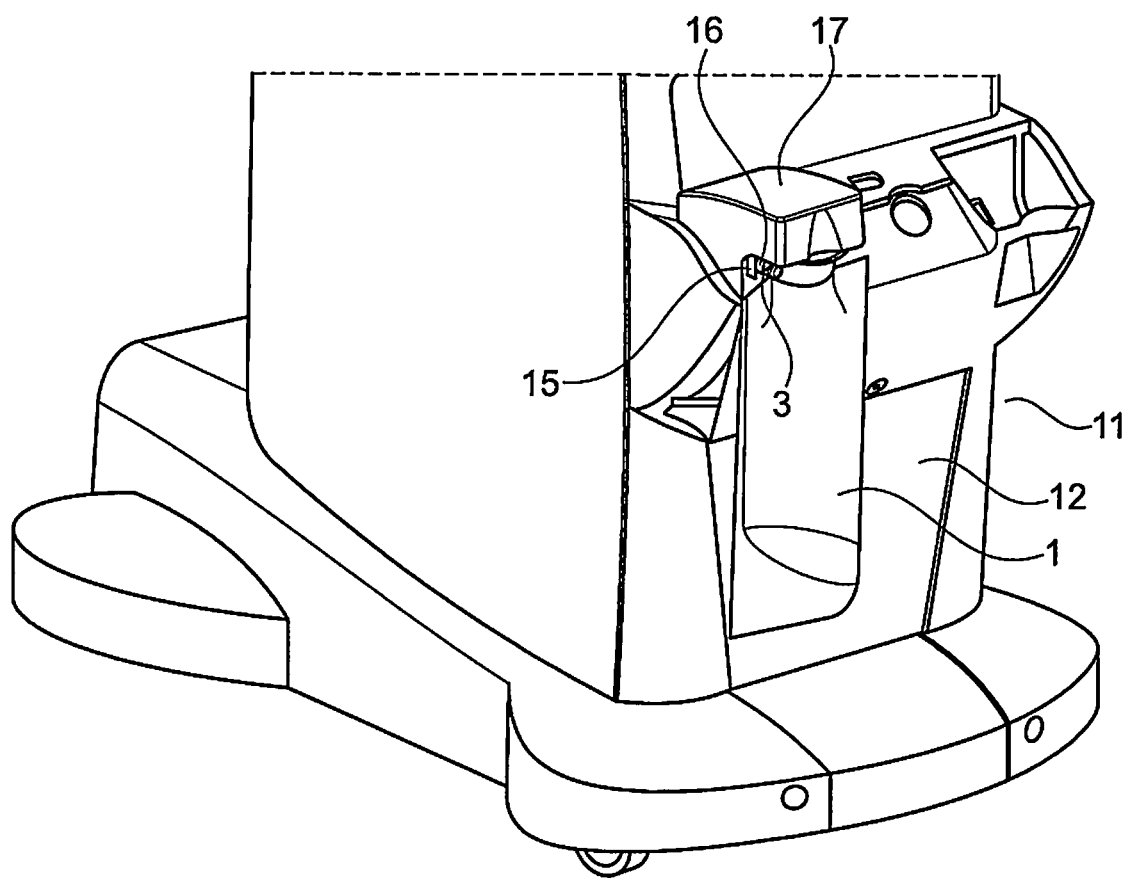
FIG. 19 shows the blood treatment device of FIG. 17 with a container attached thereto.

FIG. 19 shows the blood treatment device 11 with a container 1 attached to the attachment elements 16 of the guiding element 15. The container 1 is in a position in which it is fluidically coupled to the blood treatment device.

Figure 20:
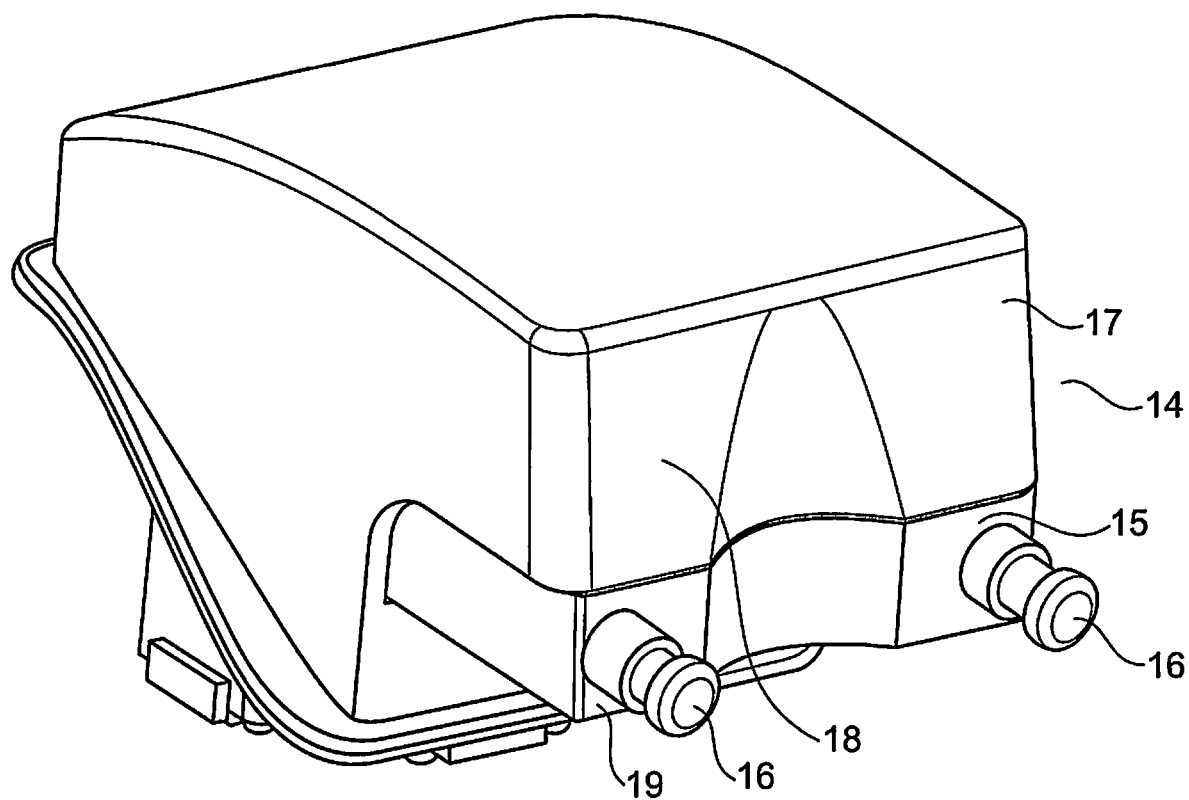
FIG. 20 shows the detailed view of the blood treatment device of FIG. 17 in which the guiding element is positioned relative to the projection portion in a closed, rinsing position.

FIG. 20 shows the attachment assembly 14 of a blood treatment device 11 in that the guiding element 15 is arranged relative to the projection portion 17 in a closed position used for rinsing the blood treatment device.

In this position, a front surface 18 of the projection portion 17 and a front surface 19 of the guiding element 15 form a continuous front surface. The rinsing position of the guiding element 15 relative to the projection portion 17 is further illustrated in a side view of the blood treatment device 11 shown in FIG. 21. From this figure it becomes especially clear, that in the closed position/rinsing position of the guiding element relative to the projection portion 17, the front end surface 18 of the projection portion 17 and the front end surface 19 of the guiding element 19 form a continuous front end surface.

Figure 21:
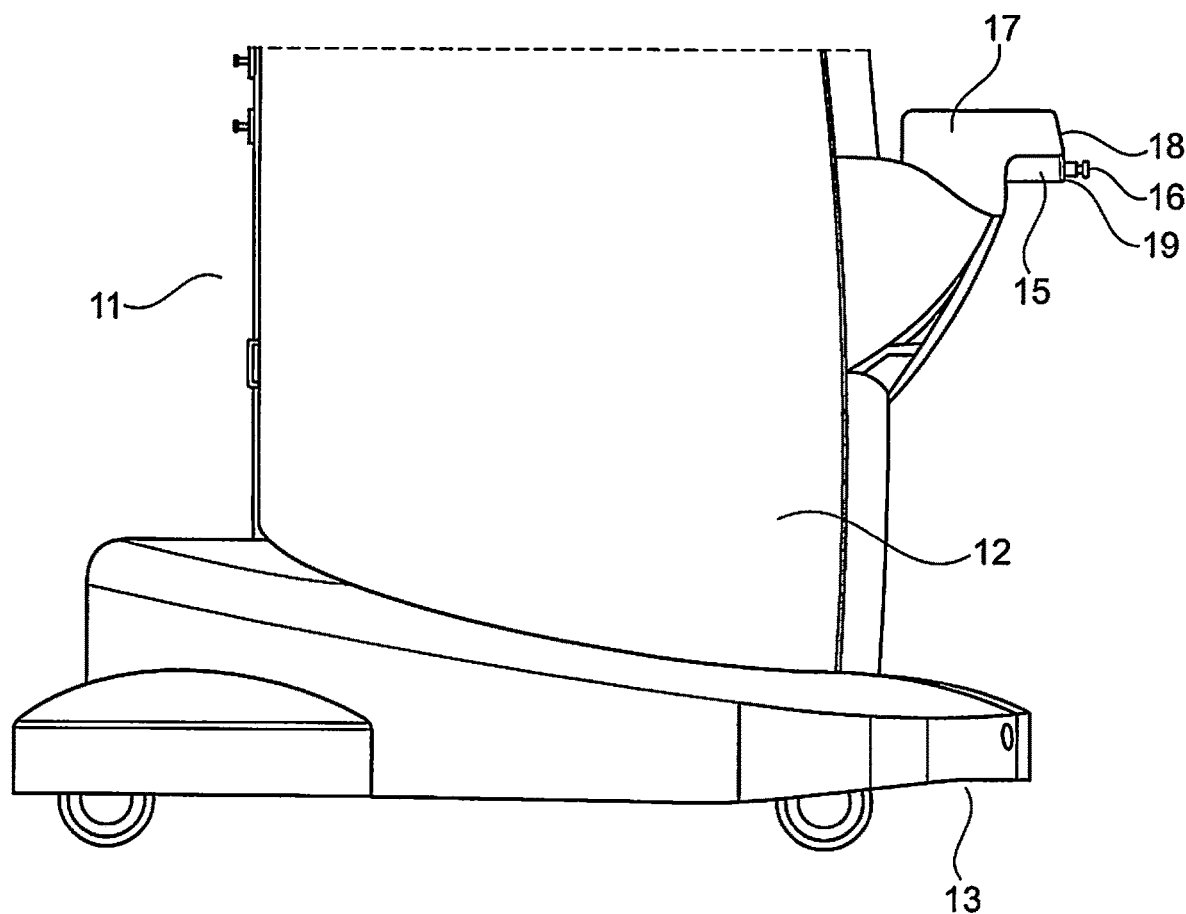
FIG. 21 shows a side view of the blood treatment machine of FIG. 17, in which the guiding element is positioned relative to the projection portion in the closed, rinsing position.
Figure 22:
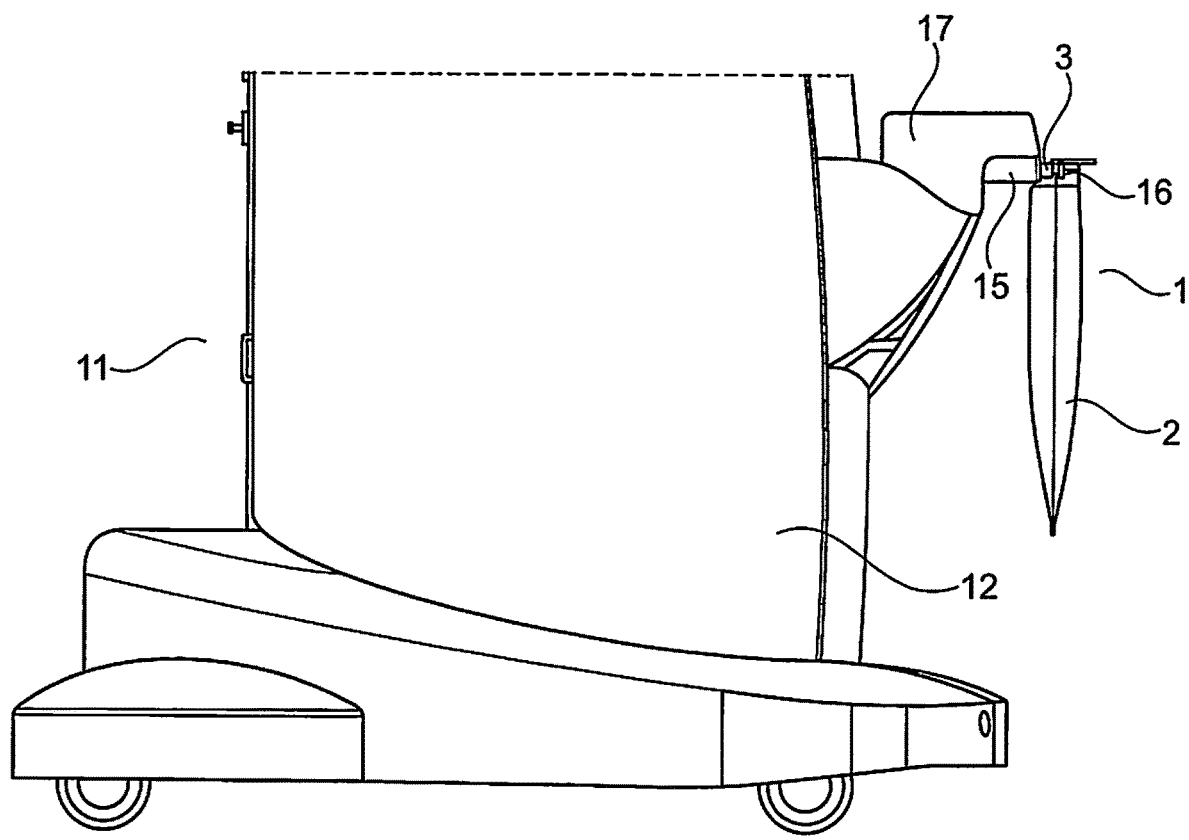
FIG. 22 shows the blood treatment device of FIG. 21, wherein a container is attached to the attachment elements of the blood treatment device.

FIG. 22 shows the blood treatment device of FIG. 21, with a container 1 being attached via its attachment elements 3 to the attachment elements 16 of the blood treatment device. This position is adopted when the blood treatment device is rinsed/disinfected by internal circulation but already prepared for the next blood treatment by the provision of the container 1. Prior to commencing the next blood treatment, the container 1 will be fluidically connected to the blood treatment device 11.

Figure 23:
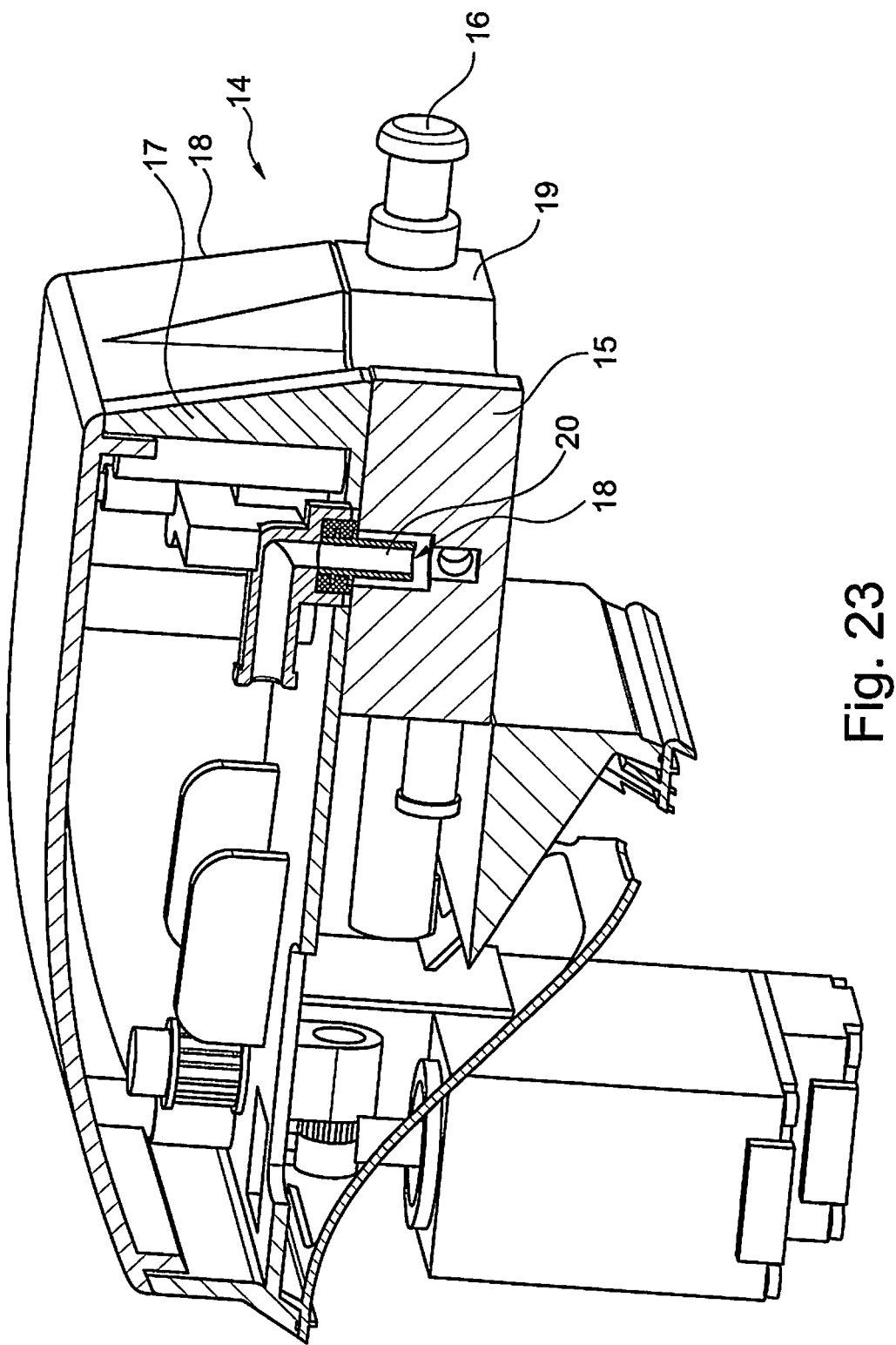
FIG. 23 shows a sectional view illustrating the rinsing position of the guiding element relative to the projection portion.

FIG. 23 illustrates in more detail the structural configuration of the attachment assembly 14 of the blood treatment device by providing a sectional view of the attachment assembly 14 in the closed/rinsing position illustrated in FIGS. 21 and 22. As can be seen in FIG. 23, the front end surfaces 18 and 19 of the projection portion 17 and the guiding element 15 provide a continuous front surface.

In this relative positioning, the connection element 20 of the blood treatment device that in the embodiment of FIG. 23 has the form of a spout used for dispensing water into the container 1 is inserted in a cavity 18 present in the guiding element 15. Thus, the internal fluidic system of the blood treatment device is closed off from the outside and rinsing fluid can be circulated within the blood treatment device without fluid leaking from the spout 17 to the outside of the blood treatment device 11.

Figure 24:
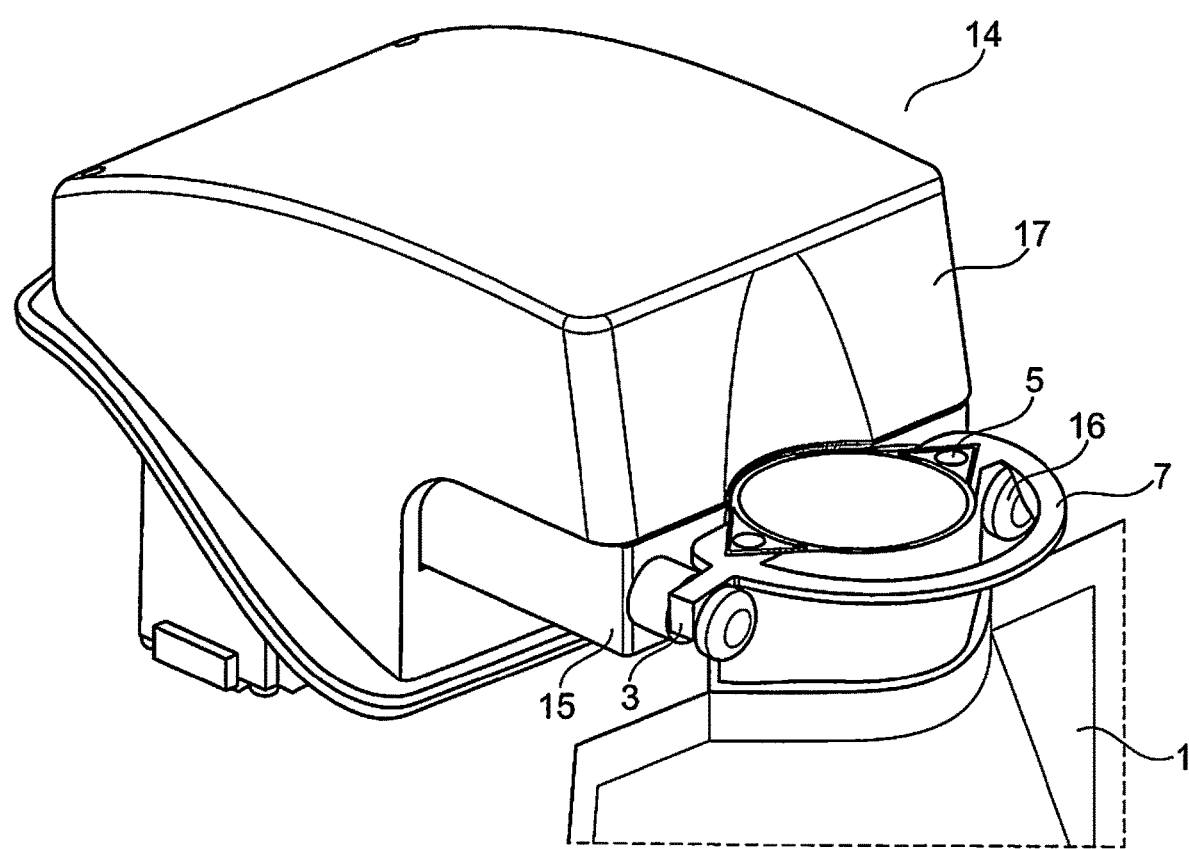
FIG. 24 shows a perspective view of the container that is attached to the attachment elements of the blood treatment device in the closed rinsing position.

FIG. 24 shows a close-up view of the connection assembly 14 of the blood treatment device 11 to that a container 1 has been attached via the attachment elements 3 and 16. The connection assembly 14 is in the closed position/rinsing position.

Figure 25:
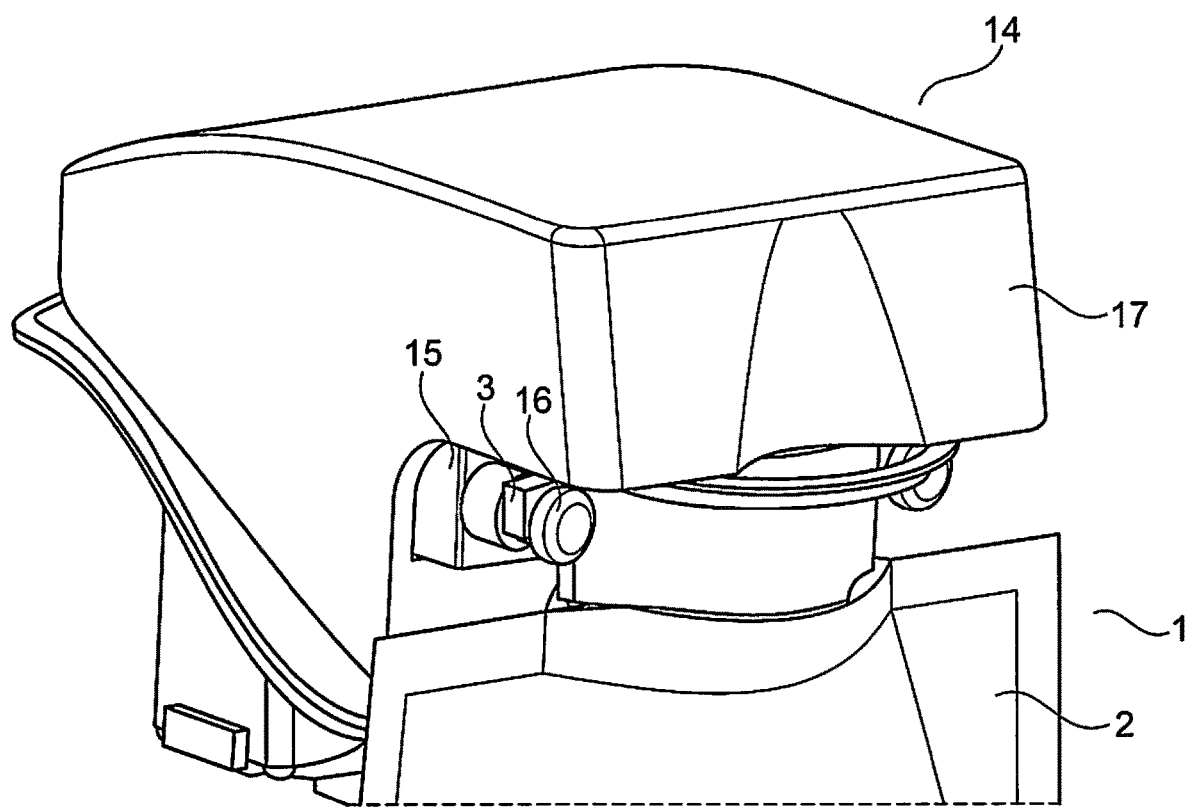
FIG. 25 shows the container connected to the blood treatment device in a position, in which the container is fluidically coupled to the blood treatment device.

In order to fluidically couple the container 1 to the connection assembly 14 and thus to the blood treatment device 11, the guiding element 15 is subsequently moved inwards towards the side surface of the blood treatment device 11, as shown in FIG. 25. The container 1 attached to the attachment element 16 of the blood treatment device 11 is thus moved towards the side surface of the blood treatment device 11 until it is arranged under the projection portion 17 and the connection elements 5 of the bag 1 are horizontally aligned with the connection elements 20 of the blood treatment device.

Figure 26:
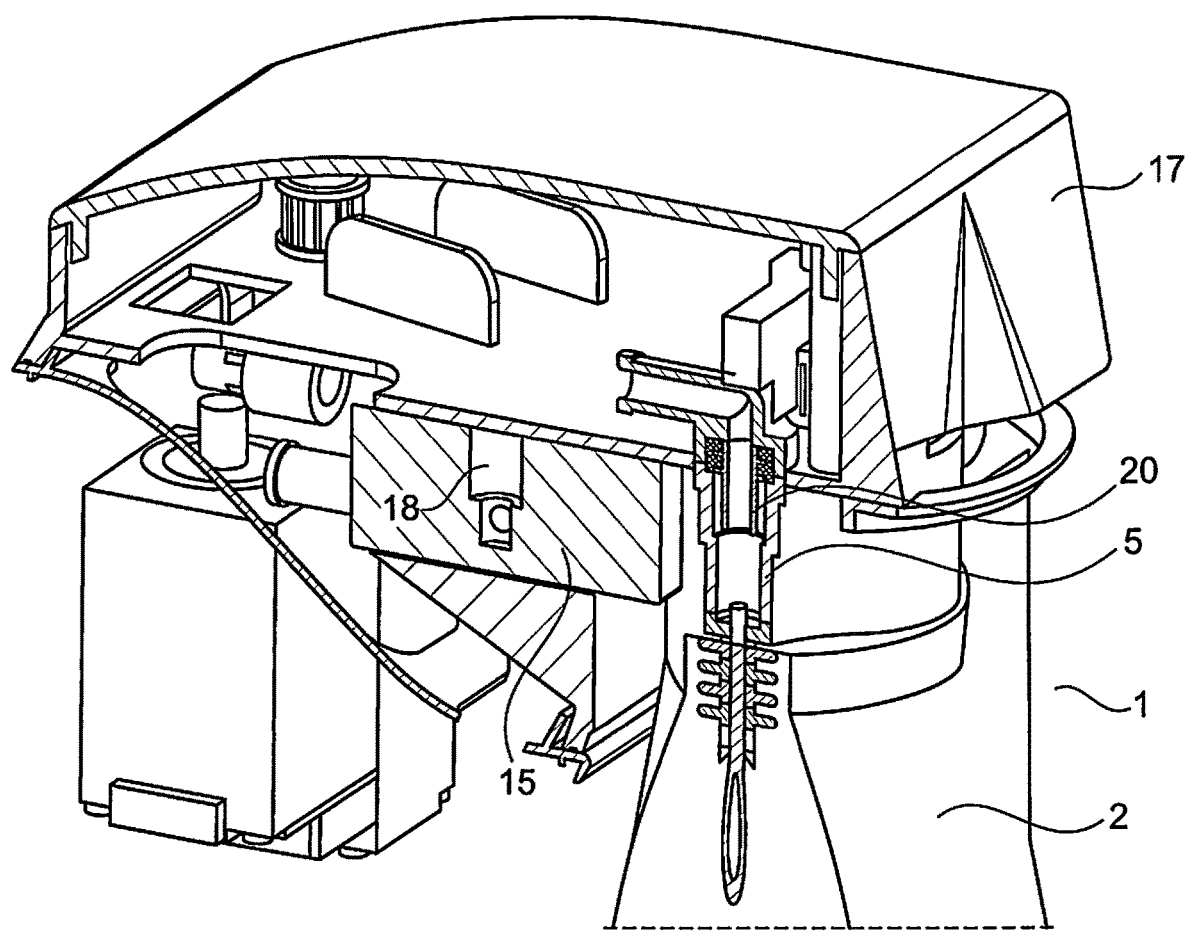
FIG. 26 shows a sectional view of the arrangement of FIG. 25.

As illustrated in FIG. 26, the guiding element 15 and thus the container 1 attached to the attachment elements 16 mounted onto the guiding element 15 are moved upwards to connect the connection elements 5 of the container 1 with the connection element 20 of the blood treatment device. Alternatively the container 1 can be held stationary by the guiding element 15 and the connection elements 20 of the blood treatment device are moved downwards to be inserted into the connection elements 5 of the container 1 to thereby fluidically couple the container 1 to the blood treatment device 11.

Figure 27:
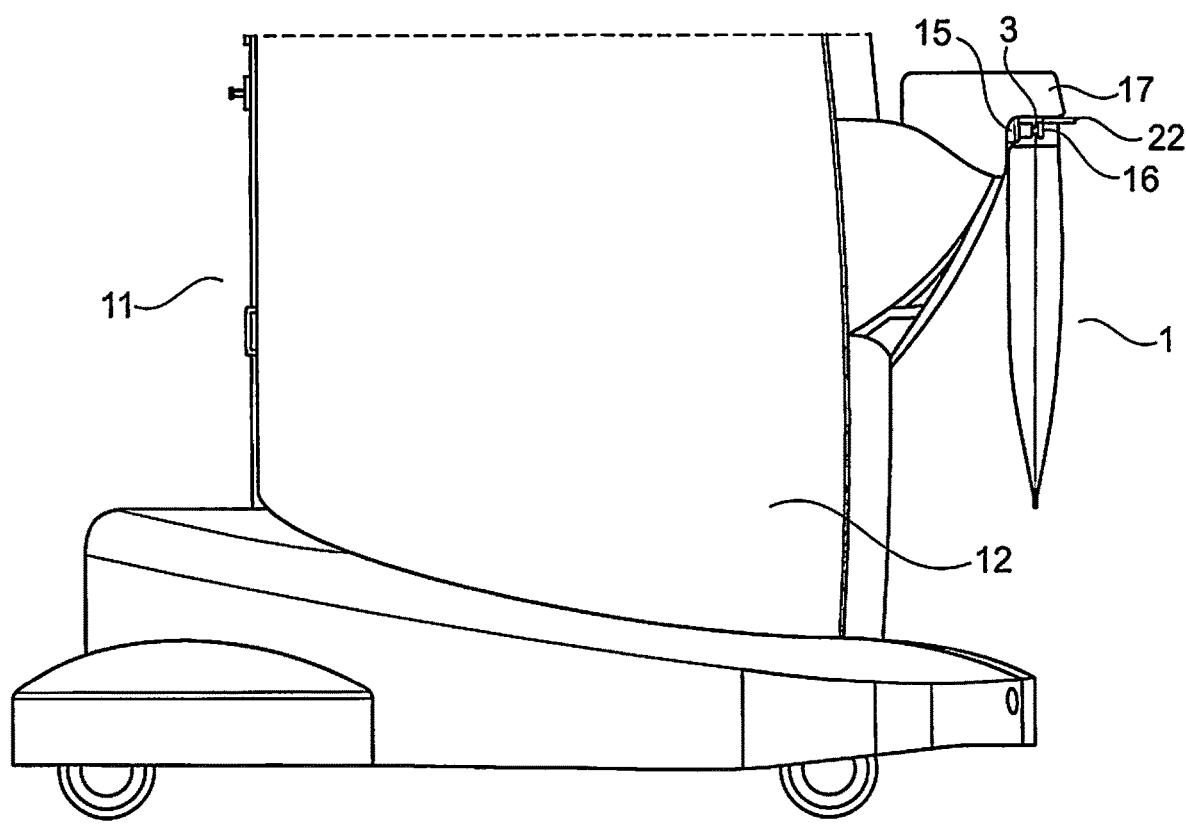
FIG. 27 shows a blood treatment device, to which a container is fluidically coupled.

FIG. 27 shows a side view of the blood treatment device with a container 1 fluidically coupled to the blood treatment device 11 in that position/relative positioning shown in FIG. 26.

Figure 28:
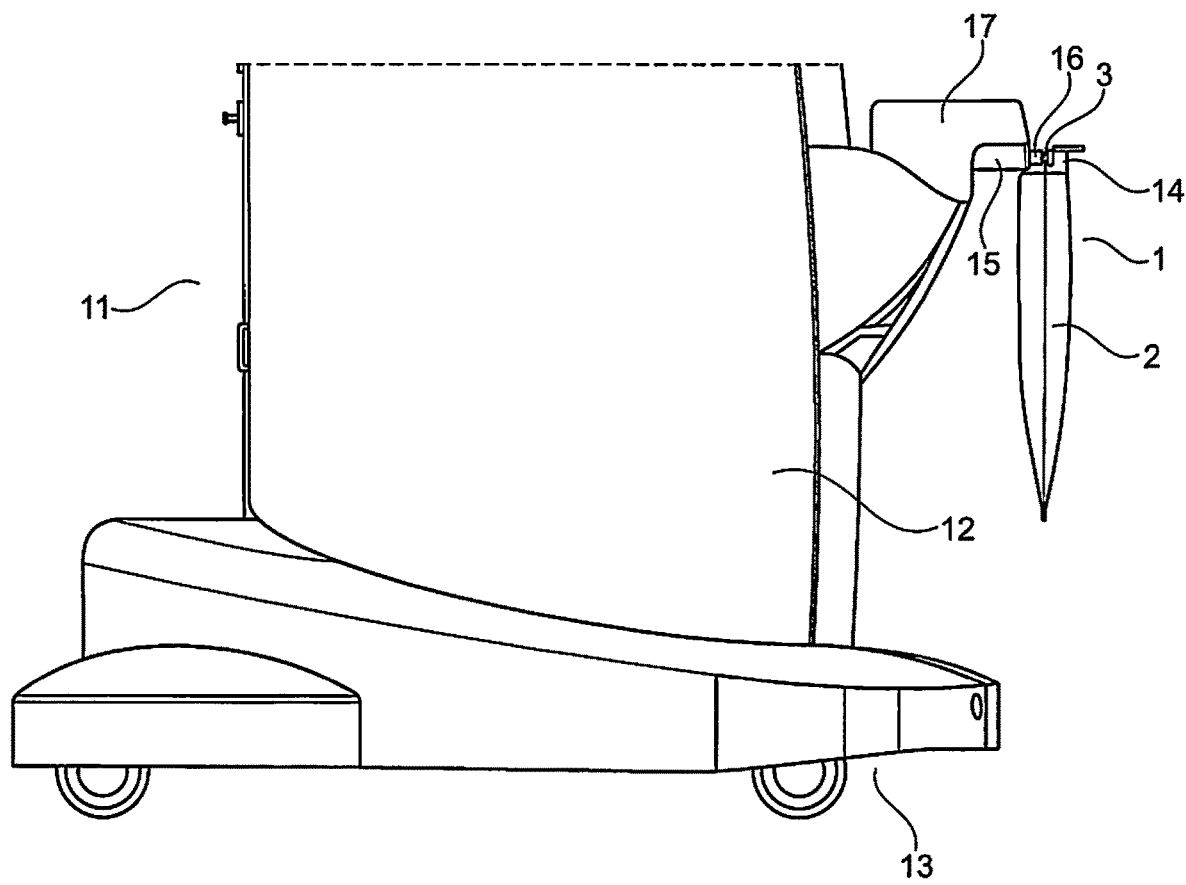
FIG. 28 shows the blood treatment device of FIG. 27 in the rinsing position.

FIG. 28 shows a side view of the blood treatment device 11 with the attachment assembly 24 being in the position shown in FIG. 24.

Figure 29:
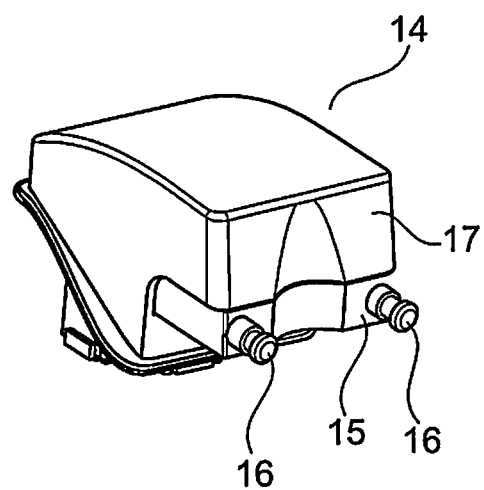
FIG. 29 shows the guiding element and the projection portion of the blood treatment device in the closed rinsing position.

FIG. 29 shows another view of the connection assembly 14 of the blood treatment device in the closed rinsing position.

Figure 30:
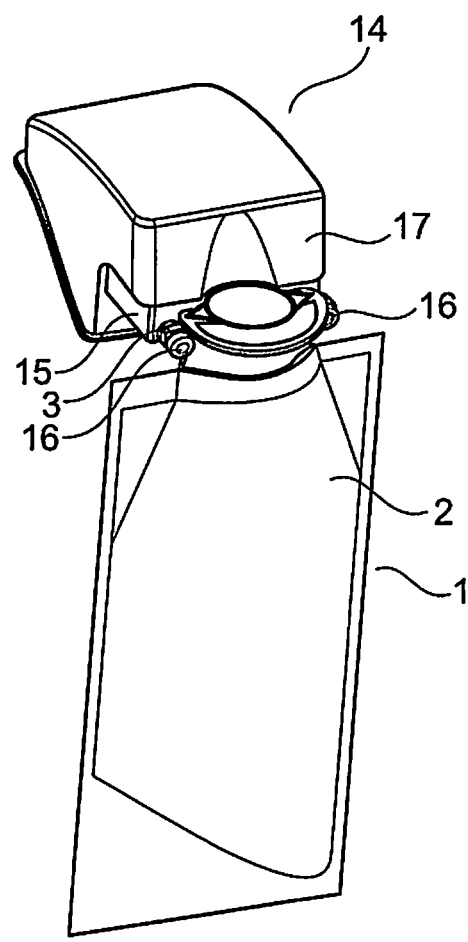
FIG. 30 shows the arrangement of FIG. 29, to which a container has been attached.

FIG. 30 shows the attachment assembly 14 of FIG. 29, wherein a container 1 has been attached via its attachment elements 3 (hook-shaped) and the attachment elements 16 (stud-shaped) of the blood treatment device. In this depiction, the attachment assembly 14 is still in the closed rinsing position.

Figure 31:
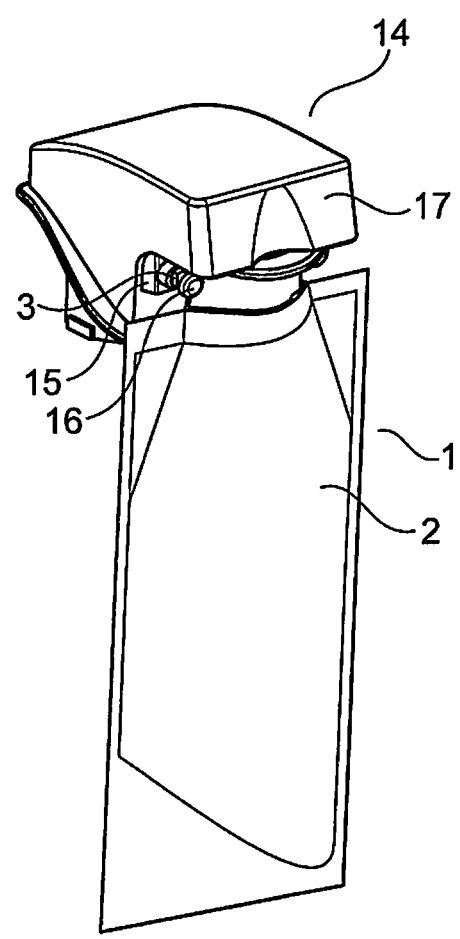
FIG. 31 shows the position, in that the container is fluidically coupled to the blood treatment device.

FIG. 31 shows the attachment assembly 14, wherein the container 1 has been moved inwards under the projection portion 17 and has been fluidically coupled to the blood treatment machine by inserting the connection elements of the blood treatment device into the connection elements of the container 1, by either moving the container 1 upwards towards the projection portion 17 or by moving the connection elements 20 of the blood treatment device downwards into the connection elements 5 of the container 1.

Next, a method of connecting a container for concentrate to a blood treatment device according to the present invention will be described.

Figure 32:
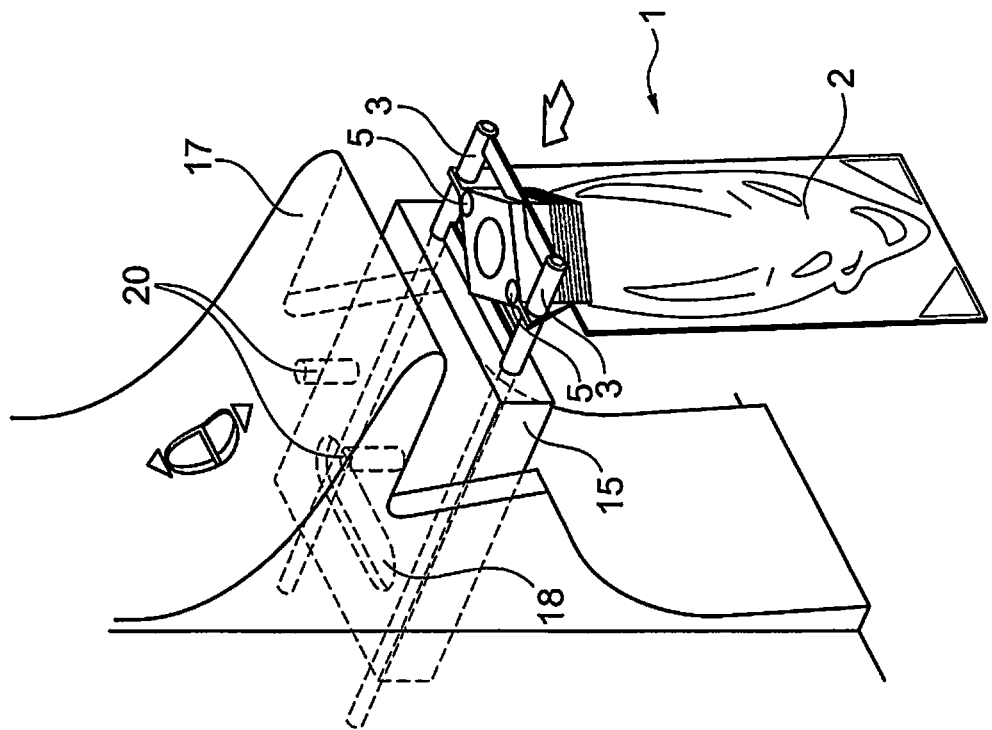
FIG. 32 shows how the container is attached to the attachment elements of the blood treatment device.

As shown in FIG. 32, the attachment elements 16 of the blood treatment device are inserted into the attachment elements 3 of the container 1. As can be seen in FIG. 32, the attachment elements 16 of the blood treatment device and the attachment element 3 of the container are configured asymmetrically to allow mounting of the container to the blood treatment device only in one correct mounting position.

Figure 33:
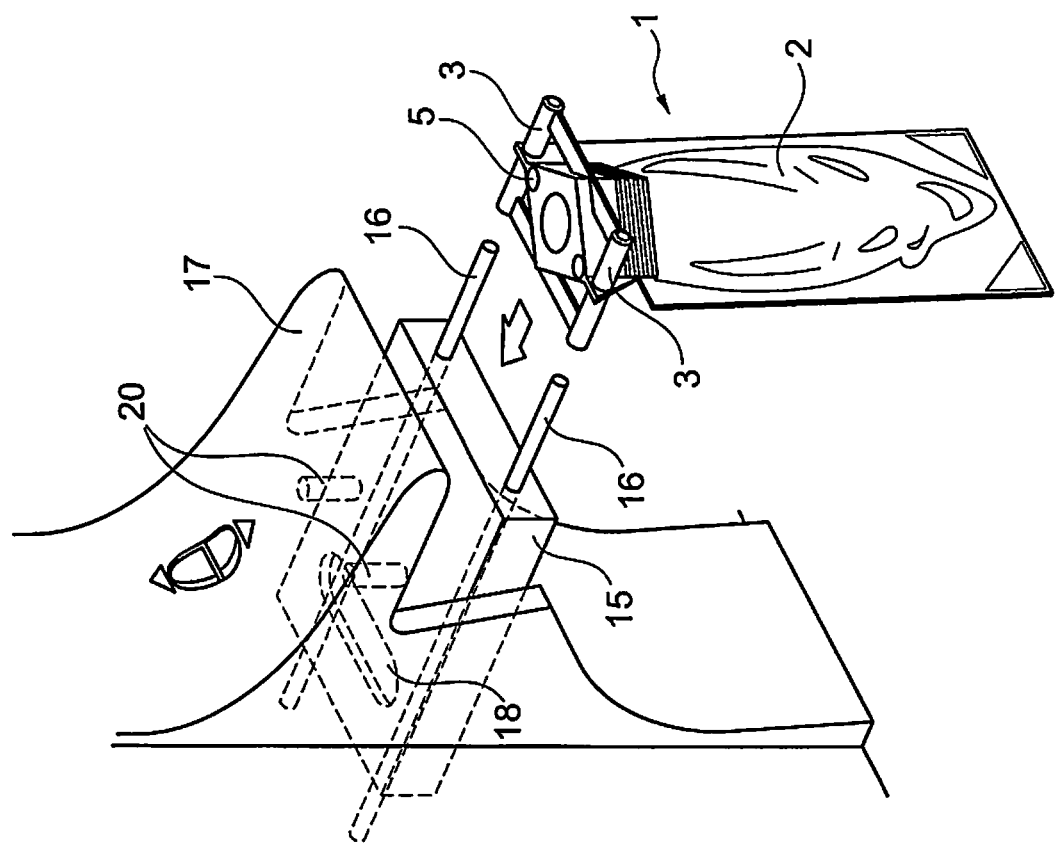
FIG. 33 illustrates how the guide element moves inwards toward the side surface of the main body of the blood treatment device to position the container in a position that it can be fluidically coupled with the connection elements of the blood treatment device.

FIG. 33 shows the container 1 connected to the attachment elements 16 of the blood treatment device via the attachment elements 3 of the container. The guiding element 15 then moves inwards in a horizontal direction toward a side surface of the blood treatment device 11 to draw the container 1 under the projection portion 17, as illustrated in FIG. 34.

Figure 34:
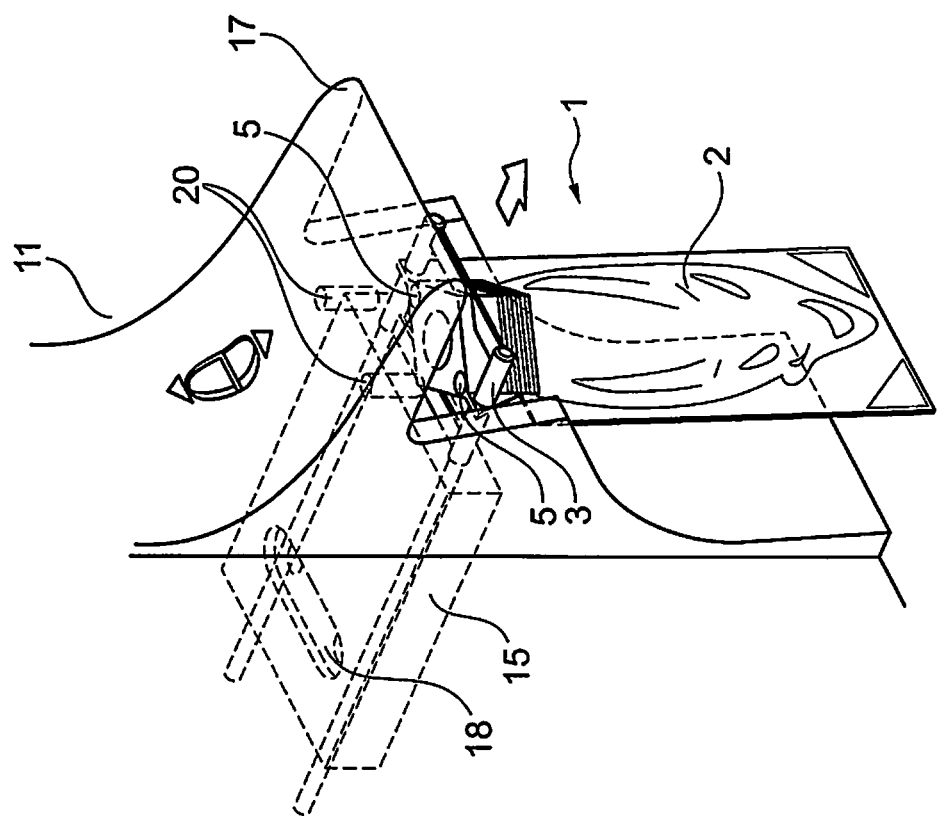
FIG. 34 shows a position in that the connection elements of the blood treatment device and the connection elements of the container are aligned in a vertical direction.

Also from FIG. 34 it can be seen that the connection elements 20 of the blood treatment device and the connection elements 5 are in this position aligned in a vertical direction so that the connection elements 20 can be inserted into the connection elements 5 of the container 1 by movement along the vertical axis.

As shown in FIG. 35, the connection elements 20 of the blood treatment device can be/are inserted into the connection elements 5 of the container 1 by moving the guiding element 15 and thus the container 1 upwards towards the projection portion 17. Alternatively, the connection elements 20 of the blood treatment device can be moved downwards to be inserted into the connection elements 5 of the container 1.

When the container 1 is fluidically coupled to the blood treatment device via the connection elements 20 and the connection elements 5 as shown in FIG. 36, treatment can be carried out by the blood treatment machine that generates the liquid concentrate from the powder concentrate contained within the main body 2 of the container 1.

After treatment has finished, the guiding element 15 and thus the container 1 attached thereto is moved downwards, as illustrated in FIG. 37. The downward movement of the container 1 is continued until the connection elements 20 of the blood treatment device are removed from the connection elements 5 of the container 1, as illustrated in FIG. 38.

The guiding element 15 and thus the container 1 attached thereto is then subsequently moved outwards in a horizontal direction similar to a drawer from the side surface of the blood treatment device 11.

As illustrated in FIG. 39, the movement of the container 1 can be paused in a position in which the container 1 is vertically aligned with the connection elements 20 of the blood treatment device, so that any droplets dripping from the connection elements 20 of the blood treatment device are caught by the container 1, preferably the connection elements 5 of the container 1.

As shown in FIG. 40, the container 1 is then moved by means of moving the guiding element 15 relative to the projection portion 17 until the container 1 is positioned further out/away from the side surface of the blood treatment device 11 than the front edge of the projection portion 17. This allows a user to easily grab the container 1.

As shown in FIG. 41, the container 1 can easily be disconnected from the attachment elements 16 of the blood treatment device by pulling the container 1 away from the blood treatment device 11.

After the container 1 has been removed, the blood treatment machine can then move the guiding element 15 upwards and/or inwards towards the side surface of the blood treatment device 11 until the connection elements 20 of the blood treatment device are aligned in a vertical direction with the cavity 18 of the guiding element 15, as shown in FIG. 42.

In this position, the blood treatment device can enter the closed/rinsing position. As shown in FIG. 43, the guiding element 15 is moved further upwards or the connection elements 20 of the blood treatment device 11 are further moved downwards, to insert the connection elements 20 into the cavity 18 of the guiding element 15 to enter the closed rinsing position.

The blood treatment machine can now be rinsed and a new concentrate bag can be attached during rinsing to the guiding element 15 by use of attachment elements 16 to commence a new treatment.

All movements of the guiding element 15 relative to the projection portion 17 can also be performed manually. For this purpose an attachment assembly 14 of a blood treatment device can comprise a lever 21 as shown in FIG. 44 or a similar structure allowing a user to manually move the guiding element relative to the projection portion 17.

FIG. 45 shows a sectional view of an embodiment in that the fluid dosing unit of a blood treatment device is equipped with an integrated valve 23 to prevent fluid from dripping from the fluid dosing unit/the connection element 20 of the fluid dosing unit if no container 1 is connected to the fluid dosing unit.

The fluid dosing unit in this example corresponds to an attachment assembly 14 discussed above. The term fluid dosing unit refers to any unit that serves to connect to a container and to dispense fluid into the container and withdraw fluid from the container in a controlled manner.

The valve comprises a valve body 24 and a valve seat 25. The valve 23 is biased in the closed position by means of a biasing element, in this embodiment by a spring 26.

In the state shown in FIG. 45, a container 1 is attached and fluidically coupled to the fluid dosing unit, so that the valve 23 is open.

FIGS. 46 and 47 show sectional views of the embodiment auf FIG. 45 in a state in that a container is connected to the fluid dosing unit and the valve is open. As shown in FIG. 46, a fluid permeable actor 27 comprising a spike 28 holds the valve 23 in the open position, so that fluid can flow through an inner lumen 29 of the fluid permeable actor 27, through the open valve 23 and through the connection element 20 of the fluid dosing unit. The connection element 20 in this embodiment corresponds to a fluid line of the fluid dosing unit. The flow path of fluid in this state is indicated by a line in FIG. 47. The valve body 24 can comprise a recess 30 for receiving the spike 28.

FIG. 48 shows sectional views of the embodiment auf FIG. 45 in a state in that no container is connected to the fluid dosing unit and the valve 23 is closed. In this state, the spring 26 is expanded and presses the valve body 24 against the valve seat 25.

FIG. 49 shows a detailed view of a fluid permeable actor 27 that can be provided at a container 1 according to the present invention to open the valve 23 of the fluid dosing unit shown in FIG. 45. The fluid permeable actor 27 comprises a spike 28 and in this embodiment four Lumina 29 for conducting fluid. The fluid permeable actor 27 comprises an outer bush/hollow cylinder 31 that defines the outer circumference of the fluid permeable actor 27. The spike 28 can be mounted onto a platform 32 that is arranged concentrically with the outer bush/hollow cylinder 31 and connected to the outer bush/hollow cylinder 31 via ribs 33. The fluid permeable actor 27 is arranged in a connection element 5 of the container. The connection element 5 can be an inlet or an outlet of the container.

FIG. 50 shows a sectional view of the fluid permeable actor 27 of FIG. 49.

The invention claimed is:

1. A container for concentrate, comprising:
a main body for containing concentrate,
a connection portion having a flat end surface facing away from the main body and an opening through which the main body can be filled with concentrate,
an inlet through which fluid can be supplied to the main body, and
an outlet through which fluid can be withdrawn from the main body,
wherein at least in the outlet a fluid permeable actor is arranged that is configured to open a valve in a fluid line of a fluid dosing unit when the container is connected to the fluid dosing unit to fluidically couple the container to the fluid dosing unit.

2. The container according to claim 1, wherein the fluid permeable actor comprises a spike configured to open the valve and at least one lumen to conduct fluid.

3. The container according to claim 1, wherein the outlet and the inlet each project along a straight line traversing the connection portion from the flat end surface facing away from the main body to a flat end surface facing the main body.

4. The container according to claim 1, wherein the container further comprises two attachment elements arranged at two opposing sides of the connection portion and configured to reversibly attach the container to two corresponding attachment elements present on a blood treatment device, wherein
the two attachment elements project in a first direction and the outlet and inlet project in a second direction that is oriented essentially at right angles to the first direction.

5. The container according to claim 1, wherein the connection portion is formed handleless and further comprises concave gripping portions.

6. A system comprising at least one container according to claim 1 and at least one fluid dosing unit,
wherein at least in a fluid line of the fluid dosing unit configured to withdraw fluid from a container connected to the fluid dosing unit, a valve is arranged that is configured to fluidically close the fluid line if no container is connected to the fluid dosing unit and further configured to be openable upon connection of a container to the fluid dosing unit to allow fluid to be withdrawn from the container through the valve.

7. The system of claim 6, wherein the at least one fluid dosing unit is a fluid dosing unit of a blood treatment device.

8. The system of claim 6, wherein the container is reversibly attached to the fluid dosing unit.

9. A method for connecting a container for concentrate to a fluid dosing unit of a blood treatment device, wherein at least in a fluid line of the fluid dosing unit configured to withdraw fluid from a container connected to the fluid dosing unit, a valve is arranged that is configured to fluidically close the fluid line if no container is connected to the fluid dosing unit and further configured to be openable upon connection of a container to the fluid dosing unit to allow fluid to be withdrawn from the container through the valve, comprising the steps:

reversibly attaching the container to the fluid dosing unit by means of attachment elements present on the container and attachment elements present on the fluid dosing unit;

moving the container and/or the fluid line of the fluid dosing unit relative to each other so that the fluid permeable actor in the outlet of the container opens the valve in the fluid line of the fluid dosing unit to fluidically couple the container to the blood treatment device.

10. The method of claim 9, wherein the container and/or the fluid line of the fluid dosing unit are moved relative to each other so that the fluid permeable actor is inserted into the fluid line to move an axially movable valve body away from a valve seat to fluidically couple the container to the fluid dosing unit.

11. The method of claim 9, wherein the container for concentrate comprises:

a main body for containing concentrate, a connection portion having a flat end surface facing away from the main body and an opening through which the main body can be filled with concentrate, a inlet through which fluid can be supplied to the main body, and an outlet through which fluid can be withdrawn from the main body, wherein at least in the outlet a fluid permeable actor is arranged that is configured to open a valve in a fluid line of a fluid dosing unit when the container is connected to the fluid dosing unit to fluidically couple the container to the fluid dosing unit.

12. A fluid dosing unit comprising a fluid line device configured to withdraw fluid from a container connected to the fluid dosing unit, and a valve arranged in the fluid line and configured to fluidically close the fluid line if no container is connected to the fluid dosing unit and further configured to be openable upon connection of a container to the fluid dosing unit by a fluid permeable actor present in an outlet of the container to allow fluid to be withdrawn from the container through the valve.

13. The fluid dosing unit according to claim 12, wherein the valve comprises an axially movable valve body that is removable from a valve seat upon connection of a container to the fluid dosing unit to allow fluid to be withdrawn from the container through the valve.

14. The fluid dosing unit of claim 12, wherein the fluid dosing unit is a fluid dosing unit of a blood treatment device.

* * * * *